US011484352B1

(12) United States Patent
Tong et al.

(10) Patent No.: US 11,484,352 B1
(45) Date of Patent: Nov. 1, 2022

(54) SURGICAL INSTRUMENT AND METHOD

(71) Applicant: Warsaw Orthopedic, Inc., Warsaw, IN (US)

(72) Inventors: Amanda D. Tong, Memphis, TN (US); Stanley T. Palmatier, Olive Branch, MS (US); Rex W. Armstrong, Cordova, TN (US); Cristian A. Capote, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/324,252

(22) Filed: May 19, 2021

(51) Int. Cl.
*A61B 17/70* (2006.01)
*A61B 17/68* (2006.01)
*A61B 17/00* (2006.01)
*A61B 90/00* (2016.01)

(52) U.S. Cl.
CPC ............. *A61B 17/7089* (2013.01); *A61B 2017/00367* (2013.01); *A61B 2017/00407* (2013.01); *A61B 2017/681* (2013.01); *A61B 2090/0811* (2016.02)

(58) Field of Classification Search
CPC ............ A61B 17/7053; A61B 17/7083; A61B 2017/00367; A61B 2017/00407
USPC ........................................................ 606/263
See application file for complete search history.

(56) References Cited

U.S. PATENT DOCUMENTS

| | | |
|---|---|---|
| 5,540,698 A | 7/1996 | Preissman |
| 8,113,410 B2 | 2/2012 | Hall et al. |
| 8,162,946 B2 | 4/2012 | Baccelli et al. |
| 8,216,245 B2 | 7/2012 | Gil et al. |
| 8,870,881 B2 | 10/2014 | Rezach et al. |
| 9,173,685 B2 | 11/2015 | Lindquist et al. |
| 9,393,063 B2 | 7/2016 | Mickiewicz et al. |
| 9,757,167 B2 | 9/2017 | Hsu et al. |
| 10,022,159 B2 | 7/2018 | Simpson |
| 10,194,954 B2 | 2/2019 | Serhan et al. |
| 10,603,078 B2 | 3/2020 | Simpson et al. |
| 10,667,845 B2 | 6/2020 | Millbrandt et al. |
| 2009/0054933 A1 | 2/2009 | Mickiewicz et al. |
| 2013/0072983 A1* | 3/2013 | Lindquist ........... A61B 17/7053 606/279 |
| 2014/0257397 A1 | 9/2014 | Akbarnia et al. |
| 2014/0257401 A1 | 9/2014 | Millan et al. |

FOREIGN PATENT DOCUMENTS

WO 2020033870 2/2020

* cited by examiner

*Primary Examiner* — Eduardo C Robert
*Assistant Examiner* — Christina Negrelli-Rodriguez
(74) *Attorney, Agent, or Firm* — Sorell, Lenna & Schmidt, LLP

(57) ABSTRACT

A surgical instrument includes a member including a body engageable with a longitudinal element to fix the longitudinal element with the body. The member further includes a distal portion having a guide including an arcuate surface being engageable with the longitudinal element. An actuator is connected with the member to incrementally tension the longitudinal element. Surgical systems, implants, spinal constructs and methods are disclosed.

18 Claims, 24 Drawing Sheets

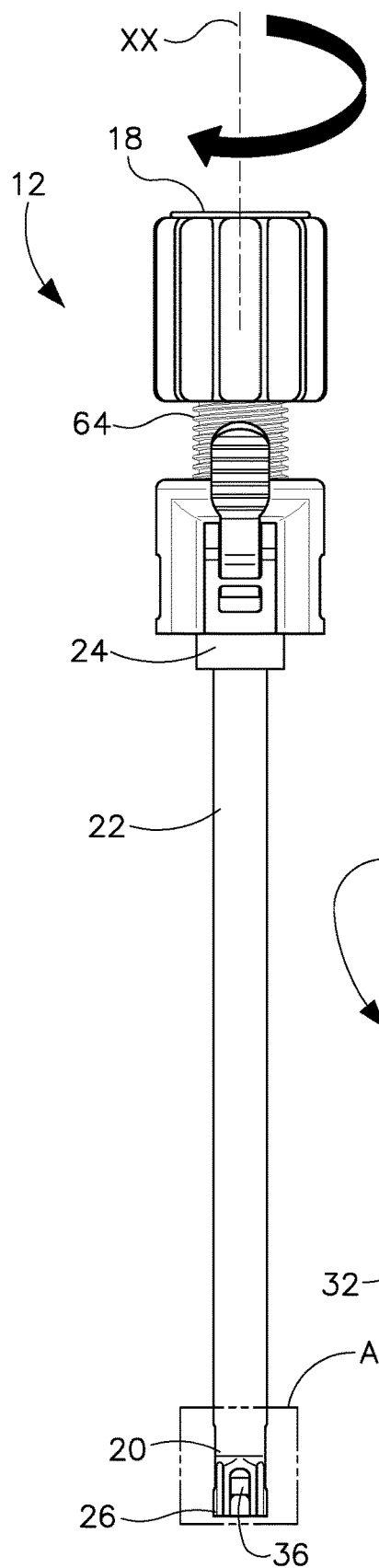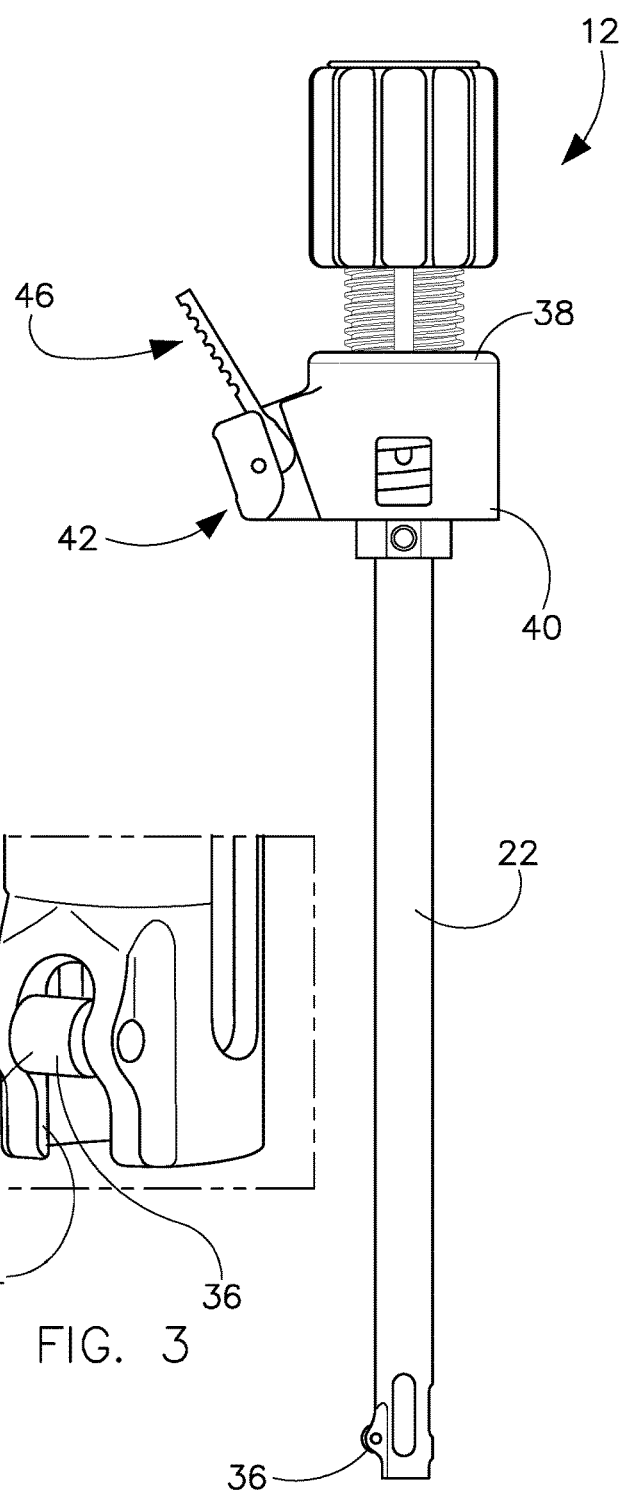

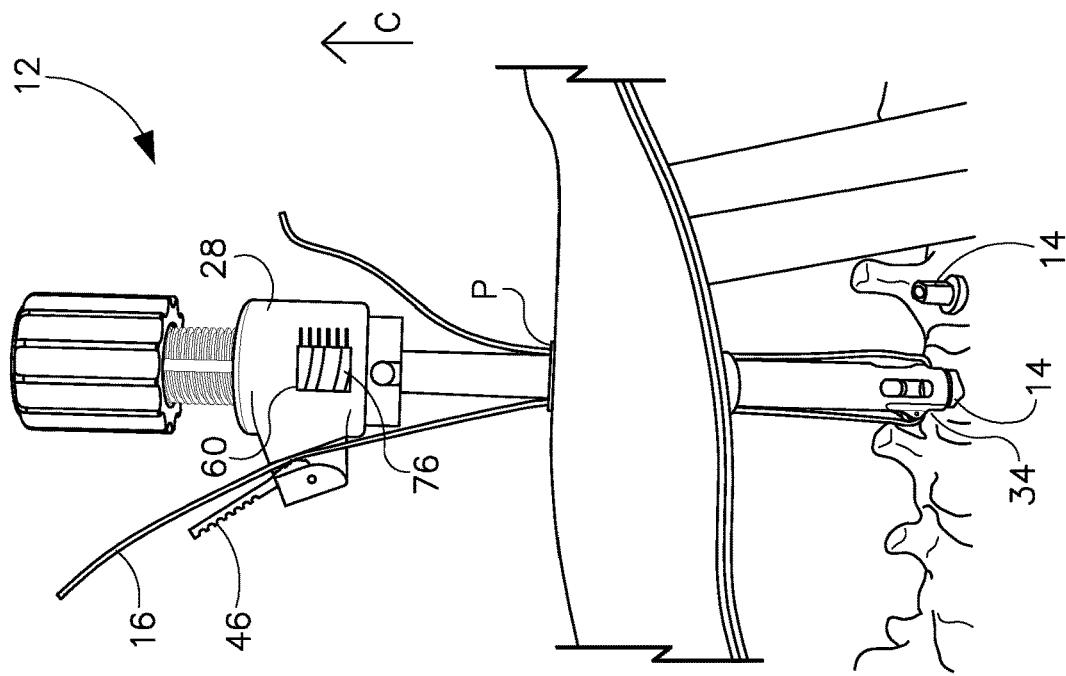
FIG. 17
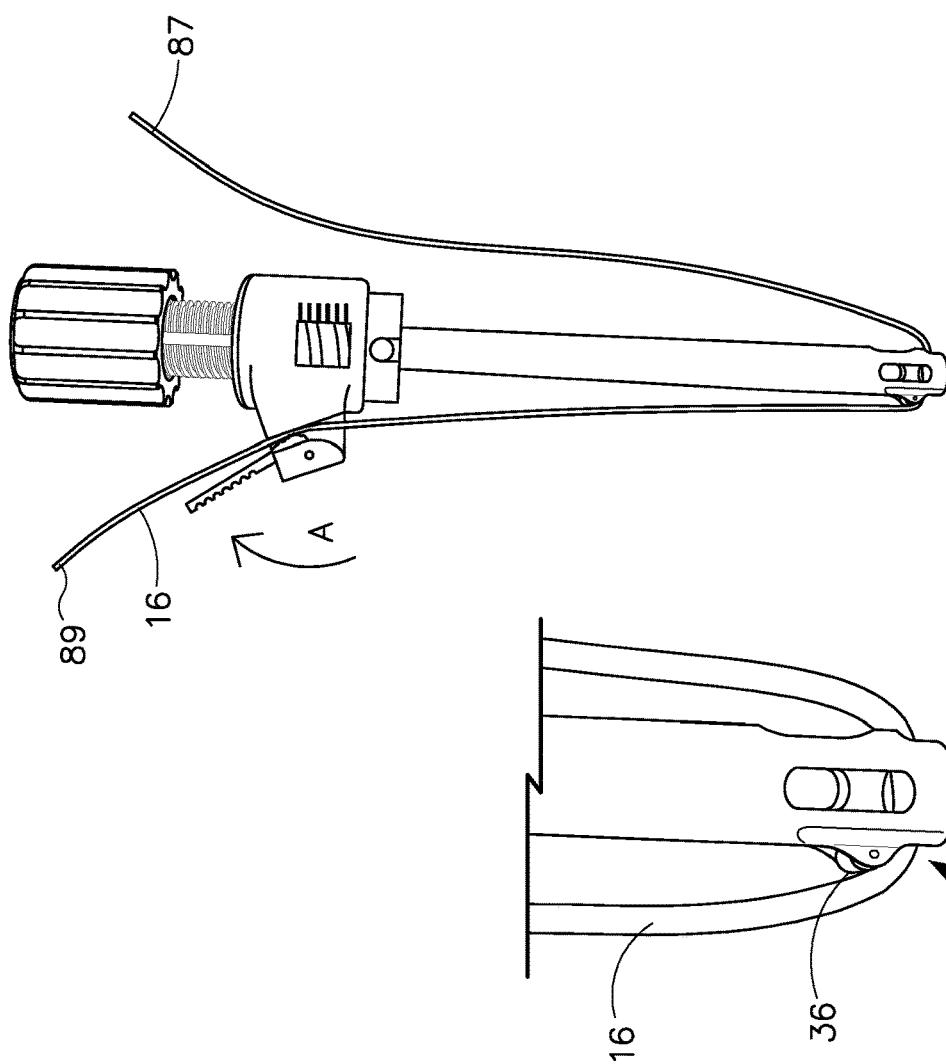
FIG. 16
FIG. 15

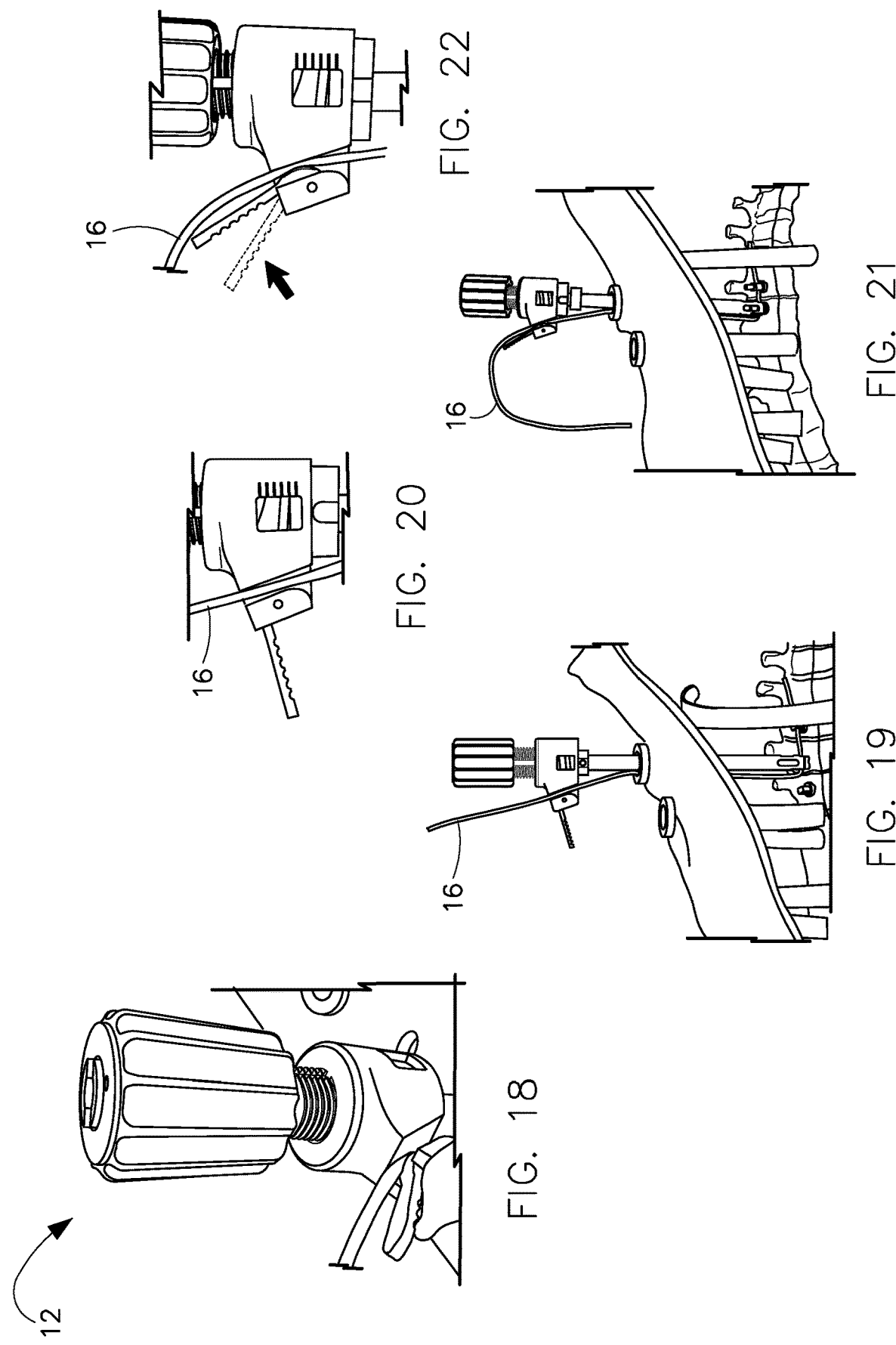

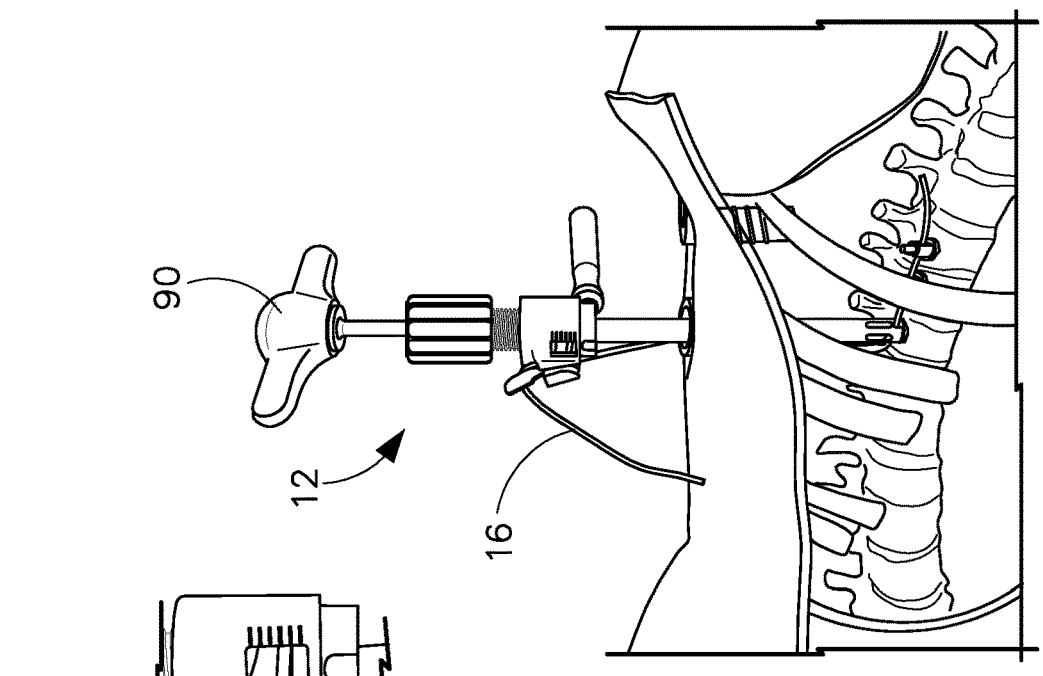
FIG. 33
FIG. 32
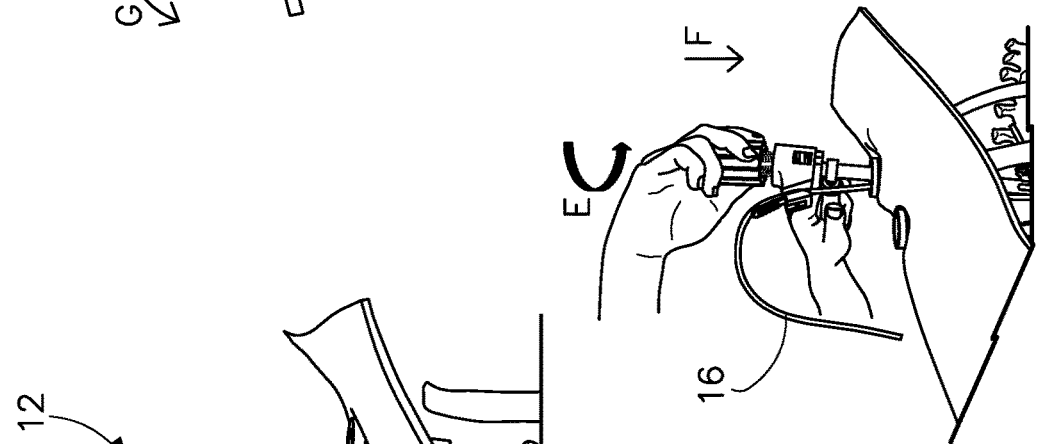
FIG. 31
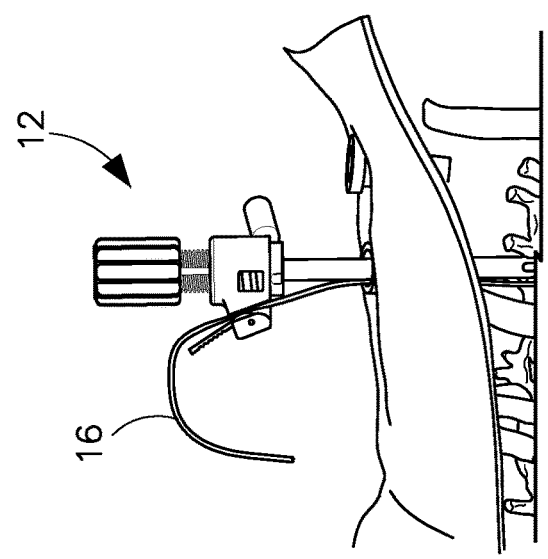
FIG. 30

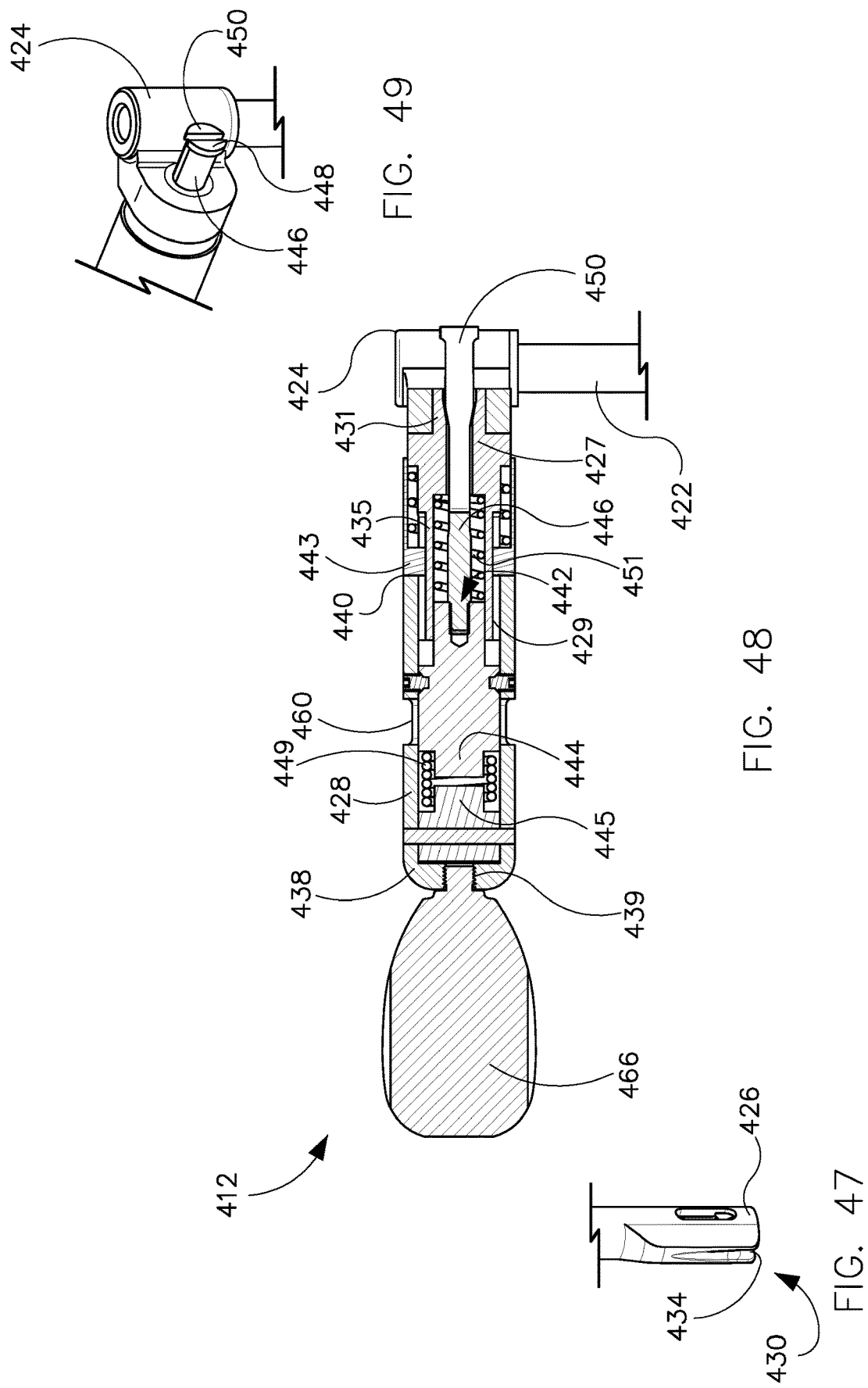

SURGICAL INSTRUMENT AND METHOD

TECHNICAL FIELD

The present disclosure generally relates to medical devices for the treatment of spinal disorders, and more particularly to a surgical instrument and method for correction of a spine disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as tethers, bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the implants for attachment to the exterior of one or more vertebral members. This disclosure describes an improvement over these prior technologies.

SUMMARY

In one embodiment, a surgical instrument is provided. The surgical instrument includes a member including a body engageable with a longitudinal element to fix the longitudinal element with the body. The member further includes a distal portion having a guide including an arcuate surface being engageable with the longitudinal element. An actuator is connected with the member to incrementally tension the longitudinal element. In some embodiments, systems, implants and methods are disclosed.

In one embodiment, the surgical instrument includes a shaft including a carriage engageable with a tether to fix the tether with the carriage. The shaft further includes a distal portion having a guide including a slot and a roller engageable with the tether. The roller is rotatable relative to the shaft to orient the tether transversely relative to the shaft and/or relative to vertebrae for disposal with one or more bone fasteners. A knob is connected with the body to incrementally tension the tether.

In one embodiment, a surgical system is provided. The surgical system includes a flexible tether and one or more bone fasteners configured for disposal with the tether. A surgical instrument includes a member including a body engageable with the tether to fix the tether with the body. The member further includes a distal portion having a guide including an arcuate surface being engageable with the tether. An actuator is connected with the member to incrementally tension the tether.

BRIEF DESCRIPTION OF THE DRAWINGS

The present disclosure will become more readily apparent from the specific description accompanied by the following drawings, in which:

FIG. 2 is a side view of the components shown in FIG. 1;
FIG. 3 is a break away view of detail AA in FIG. 2;
FIG. 4 is a side view of the components shown in FIG. 1;
FIG. 15 is a break away view of components of the system shown in FIG. 1;
FIG. 16 is a perspective view of the components shown in FIG. 1;
FIG. 17 is a perspective view of the components shown in FIG. 1 disposed with a patient body;
FIG. 18 is a break away view of components of the system shown in FIG. 1;
FIG. 19 is a perspective view of the components shown in FIG. 1 disposed with a patient body;
FIG. 20 is a break away view of components of the system shown in FIG. 1;
FIG. 21 is a perspective view of the components shown in FIG. 1 disposed with a patient body;
FIG. 22 is a break away view of components of the system shown in FIG. 1;
FIG. 30 is a perspective view of the components shown in FIG. 1 disposed with a patient body;
FIG. 31 is a perspective view of components of the system shown in FIG. 1 disposed with a patient body;
FIG. 32 is a break away view of components of the system shown in FIG. 1;
FIG. 33 is a perspective view of the components shown in FIG. 1 disposed with a patient body.

FIG. 47 is a break away view of components of the system shown in FIG. 46;

FIG. 48 is a cross sectional break away view of components of the system shown in FIG. 46;

FIG. 49 is a break away view of components of the system shown in FIG. 46;

DETAILED DESCRIPTION

Figure 1:
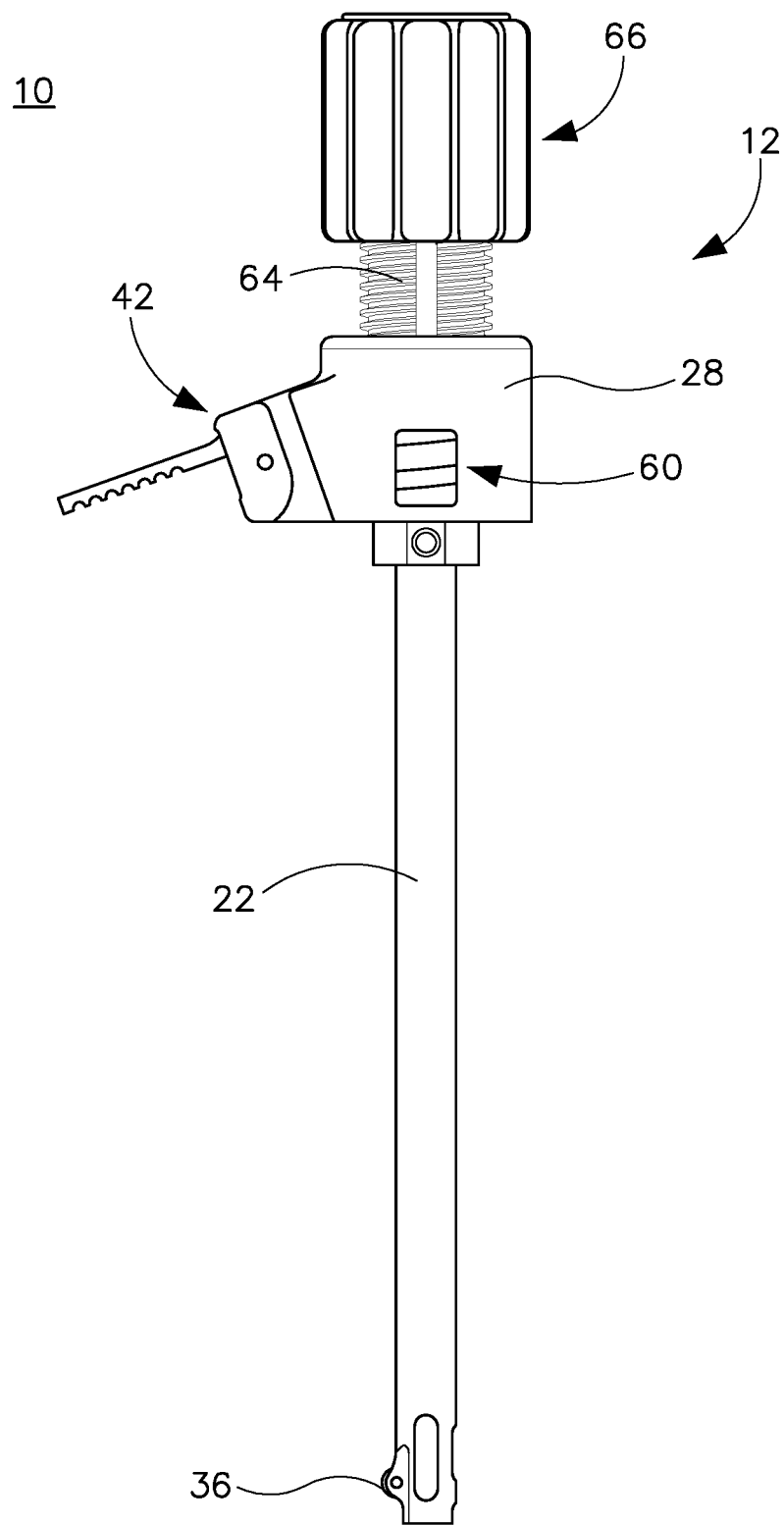
FIG. 1 is a side view of one embodiment of components of a surgical system in accordance with the principles of the present disclosure.

The exemplary embodiments of a surgical system and related methods of use are discussed in terms of medical devices for the treatment of musculoskeletal disorders and more particularly, in terms of a surgical system and method for correction of a spine disorder. In some embodiments, the surgical system may be employed in applications for correction of deformities, such as scoliosis and kyphosis. In some embodiments, the surgical system includes a surgical instrument, for example, a surgical tensioner. In some embodiments, the surgical tensioner tensions a tether that engages with one or more bone fasteners to facilitate tension between the one or more bone fasteners through a thoracoscopic port. In some embodiments, the thoracoscopic port includes a port that is inserted through a thoracic cavity of a patient to access vertebral bodies of the thoracic spine. In some embodiments, the surgical tensioner facilitates movement of at least two vertebral bodies together that are connected by a tether.

In some embodiments, the present surgical system includes a surgical instrument, for example, a surgical tensioner configured for use with a tether. In some embodiments, the tether is connected with bone fasteners, for example, vertebral body screws that are positioned laterally in a thoracoscopic approach relative to the spine. In some embodiments, the tether is tensioned with a pulling force applied to the tether via the surgical tensioner. In some embodiments, the surgical tensioner engages with one or more bone fasteners at a distal end. In some embodiments, the surgical tensioner is employed in an application for anterior vertebral body tethering that utilizes a patient's remaining skeletal growth, including growth modulation to treat scoliotic curves in late juvenile and early adolescent pediatric patients that are skeletally immature. In some embodiments, the components of the present surgical system are employed with one or more implants inserted laterally, via a thoracoscopic approach into vertebral bodies of the thoracic spine. In some embodiments, the components of the present surgical system limit additional progression of the scoliotic curve, provide correction of the thoracic spine, and/or allow for continued growth of the spine while patient mobility is maintained.

In some embodiments, the present surgical system includes one or more plates, one or more bone fasteners, including fixed angle screws, a tether, including a braided tether, and break-off set screws.

In some embodiments, the present surgical system includes a surgical tensioner that is configured to combine counter torque and a threaded mechanism to apply tension to a tether. In some embodiments, the tether includes a braid. In some embodiments, the surgical tensioner includes a threaded knob. In some embodiments, the threaded knob is engageable with a threaded cylindrical member. In some embodiments, the threaded cylindrical member includes a flange and is rotated in a direction to translate the flange to tension the tether. In some embodiments, the flange is translated in an upward and/or a downward direction. In some embodiments, the surgical tensioner includes a carriage. In some embodiments, the carriage engages the threaded cylindrical member. In some embodiments, the carriage includes a cam that is configured to grip and retain the tether. In some embodiments, the carriage includes a locking mechanism. In some embodiments, the carriage includes a cavity for disposal of a portion of the tether. In some embodiments, the carriage includes a window that is defined from a surface of the carriage. In some embodiments, the window includes an indicator window having visual indicia, including a plurality of markings disposed adjacent the indicator window. In some embodiments, the surgical tensioner includes a biasing member, for example, a spring that is disposed about the threaded cylindrical member and is disposed within the carriage. In some embodiments, the spring compresses once slack is removed from the tether or the tether is taut, and the compression of the spring facilitates translation of the flange relative to the window and the plurality of markings. In some embodiments, a shaft of the tensioner includes a counter torque for a bone fastener, for example, for set screw placement. In some embodiments, the surgical tensioner includes a roller disposed at a distal end of the surgical tensioner. In some embodiments, the roller facilitates translation of the tether at the distal end during tensioning. In some embodiments, the surgical tensioner includes a handle. In some embodiments, the handle is threaded at an end to threadingly engage with an opening in the tensioner. In some embodiments, the handle is fabricated from silicone. In some embodiments, the handle is configured for use as a counter torque. In some embodiments, the handle is employed for one or more corrective maneuvers, including compression and/or derotation when employed with an additional counter torque component.

In some embodiments, the present surgical system includes a surgical tensioner that is configured to combine counter torque via the shaft and a threaded mechanism to apply tension to a tether. In some embodiments, the surgical tensioner includes a knob, a carriage including a cam, a threaded cylindrical member including a flange, a spring and a roller. In some embodiments, the knob is configured to engage a threaded surface of the threaded cylindrical member. In some embodiments, the carriage is configured to engage mating slots of the threaded cylindrical member. In some embodiments, the mating slots are longitudinal mating slots. In some embodiments, the spring is disposed around the threaded cylindrical member and is disposed within the carriage. In some embodiments, the carriage includes a window. In some embodiments, the carriage includes indicia, for example, a plurality of markings. In some embodiments, an end of the tether is disposed with a locking mechanism of the carriage. In some embodiments, the locking mechanism includes a cam. In some embodiments, the locking mechanism is a single tether gripper. In some embodiments, the locking mechanism is oriented between an open/non-locked orientation and a closed/locked orientation. In some embodiments, a portion of the tether is attached to an end of the shaft and engages with the roller. In some embodiments, the knob is rotated and the carriage is translated to tension the tether. In some embodiments, the window, the spring, the flange and the plurality of markings indicate threaded cylindrical member positioning relative to the plurality of markings. In some embodiments, applied tension is indicated via carriage positioning. In some embodiments, the plurality of markings include laser-marked lines. In some embodiments, the spring compresses once the tether is taut. In some embodiments, the shaft of the surgical tensioner includes a threaded hole configured for connection with a handle. In some embodiments, the handle is oriented in two positions relative to the shaft. In some embodiments, the roller facilitates translation of the tether during tensioning.

In some embodiments, the present surgical system includes a surgical instrument, including a surgical tensioner that is employed with a method that includes the step of assembling a threaded handle to a shaft of the surgical tensioner. In some embodiments, the handle is threaded and is disposed with a threaded opening defined from a surface of the shaft. In some embodiments, the method includes the step of disposing the tether through a thoracoscopic port. In some embodiments, the method includes the step of inserting the surgical tensioner into the port and docking the surgical tensioner with a fixed angle screw. In some embodiments, the method includes the step of aligning the tether with a tensioner roller of the surgical tensioner. In some embodiments, the method includes the step of disposing the tether with a cavity of a carriage of the surgical tensioner. In some embodiments, a locking mechanism of the carriage is placed in an open/non-locked orientation to dispose a portion of the tether with the cavity and the locking mechanism is disposed in a closed/locked orientation to secure the tether with the carriage. In some embodiments, the tether is tensioned by rotating a knob of the surgical tensioner in a clockwise direction. In some embodiments, when the knob is rotated, the knob facilitates translation in an upward direction of a threaded cylindrical member and the carriage. In some embodiments, the method includes the step of indicating tension. In some embodiments, the threaded cylindrical member translates relative to a plurality of indicia markings and a biasing member, for example, a spring that is compressed to indicate tensioning of the tether. In some embodiments, the method includes the step of securing the tether with a set screw. In some embodiments, the set screw is provisionally tightened via a driver that is configured for disposal through the shaft of the surgical tensioner. In some embodiments, the method includes the step of releasing tension from the tether once the tether is disposed with the fixed angle screw. In some embodiments, the knob is rotated in a counterclockwise direction. In some embodiments, the method includes the step of releasing the tether. In some embodiments, the locking mechanism is positioned in the open/non-locked orientation to release or adjust the tether.

In some embodiments, the present surgical system includes a surgical instrument, including a surgical tensioner that is configured for segmental tensioning of a tether. In some embodiments, the surgical instrument is employed with a method that includes the step of positioning the tether relative to the tensioner. In some embodiments, a threaded handle of the tensioner is assembled with a shaft of the tensioner in a selected orientation. In some embodiments, the tether is inserted through a selected port via a tether slot disposed on a distal end of the surgical tensioner. In some embodiments, the tether is inserted through a selected port via a shaft of the surgical tensioner. In some embodiments, a user grasps an end of the tether during insertion of the tether with the surgical tensioner. In some embodiments, the surgical tensioner coupled with the tether is positioned onto the fixed angle screw until fully seated. In some embodiments, the tether is provisionally tightened at a first vertebral level with a provisional set screw driver. In some embodiments, the position of the set screw relative to the fixed angle screw can be viewed through a window disposed within a carriage of the tensioner. In some embodiments, the method includes the step of placing the tether in an adjacent fixed angle screw. In some embodiments, the tether is positioned into the subsequent fixed angle screw within the same port. In some embodiments, the tether is positioned with an adjacent fixed angle screw via a braid grasper instrument and the shaft of the tensioner. In some embodiments, the tether is positioned with an adjacent fixed angle screw. In some embodiments, the user grasps a free end of the tether to place the tether into a taut orientation, and the slot of the surgical tensioner translates the tether into the fixed angle screw.

In some embodiments, the present surgical system includes a surgical tensioner which provides a global tensioning of a tether used with a plurality of bone fasteners, for example, fixed angle screws. In some embodiments, to apply segmental tensioning to the tether, the surgical tensioner is inserted into the surgical site via a port. In some embodiments, the surgical tensioner is positioned into a first orientation, for example, a starting orientation where the knob is disposed in a fully non-threaded orientation with a threaded cylindrical member of the surgical tensioner. To position the knob in the fully non-threaded orientation, the knob is rotated in a counterclockwise direction for disposal at a proximal portion of the threaded cylindrical member. In some embodiments, the tether is disposed with the surgical tensioner. In some embodiments, the tether is loaded into a cavity of a carriage of the surgical tensioner. In some embodiments, the carriage includes a locking mechanism that includes a cam. In some embodiments, the locking mechanism is oriented into an open/non-locked orientation. In some embodiments, a user grasps the tether and orients the tether into a taut configuration to dispose the tether into the cavity of the carriage. In some embodiments, the user visually and/or tactilely confirms that the tether is fully seated within the cavity and is engaged by the locking mechanism. In some embodiments, to maintain engagement between the locking mechanism and the tether, a user grasps the carriage until initial tension is applied to the tether. In some embodiments, the tether can be pre-tensioned. In some embodiments, to pre-tension the tether, the knob is rotated about two full rotations, and while the user maintains the tether in a taut configuration, the carriage is pushed down as the tether is loaded into the cavity of the carriage. In some embodiments, the carriage is translated in a downward direction and the tether is disposed into the cavity of the carriage.

In some embodiments, the surgical tensioner described above applies tension to the tether and the tension is gauged. In some embodiments, a selected amount of tension is applied to the tether between adjacent fixed angle screws by rotating the knob in a clockwise direction. In some embodiments, initial rotation of the knob will remove slack from the tether before tensioning occurs. In some embodiments, a roller at a distal end of the surgical tensioner facilitates translation of the tether during tensioning. In some embodiments, relative tension is gauged by the position of a flange of the threaded cylindrical member relative to laser-marked indicia markings. In some embodiments, relative tension on the tether is indicated when slack is removed from the tether and an internal spring compresses. In some embodiments, a set screw is provisionally tightened to secure the tether with a fixed angle screw. In some embodiments, the tether is secured with the fixed angle screw via a set screw. In some embodiments, a driver is employed to tighten the set screw and the driver is disposed and translates through a shaft of the surgical tensioner. In some embodiments, the driver is removed from the shaft of the tensioner. In some embodiments, the knob is rotated in a counterclockwise direction to place the tensioner into the first orientation described above. In some embodiments, the tether is released from the locking mechanism and the surgical tensioner is removed from the fixed angle screw.

In some embodiments, the surgical tensioner is employed to dispose the tether with a plurality of fixed angle screws disposed at adjacent vertebral levels and to tension the tether between each fixed angle screw. In some embodiments, the plurality of fixed angle screws and the adjacent vertebral levels can be accessed by the same port. In some embodiments, the adjacent vertebral levels can be accessed via a different port. In some embodiments, the surgical tensioner is moved to a second port. In some embodiments, a braid grasper instrument is employed to transfer the tether to the subsequent port. In some embodiments, the carriage of the surgical tensioner may translate to a bottom surface and/or end position corresponding to a first tension on the tether of the knob and additional tension can be applied to the tether. For example, the set screw can be provisionally tightened to secure the tether such that the first tension is maintained. The knob is rotated in the counterclockwise direction to dispose the carriage in an initial and/or starting orientation. The cam is unlocked, the tether is pulled taut and the tether is re-disposed into the cavity of the carriage. The knob is rotated in the clockwise direction to return the flange to a position corresponding to the first tension on the tether. The driver is inserted into the shaft of the surgical tensioner to remove the set screw from the fixed angle screw/driver and the knob is rotated in the clockwise direction to apply additional and/or a second tension to the tether. In some embodiments, upon application of the second tension on the tether, the set screw can be tightened with the driver to fix the tether with the fixed angle screw. In some embodiments, the surgical tensioner can be used to apply additional correction. In some embodiments, after achieving the selected correction and appropriate tether tension, a break-off driver can be employed and disposed through the surgical tensioner, or the counter torque can be employed to complete the tightening of the set screw and to break-off the set screw at each vertebral level.

In some embodiments, the present surgical system includes a surgical tensioner configured to tension a tether between adjacent fixed angle screws. In some embodiments, a thoracoscopic port is employed. In some embodiments, the port is 15 mm in diameter. In some embodiments, the tensioner includes an actuator, for example, a knob to apply tension to the tether and an indicator. In some embodiments, the tensioner includes a tether gripping mechanism, provides a screw connection, and/or provisionally tightens a set screw with the fixed angle screw.

In some embodiments, the present surgical system includes a surgical tensioner which includes a gripper portion for engaging with a tether. In some embodiments, the tensioner includes a counter torque mechanism, including a shaft and a threaded mechanism, including a threaded cylindrical member to apply tension to the tether. In some embodiments, the tensioner includes two spring loaded cams. In some embodiments, a knob engages with a threaded cylindrical member and is rotated in a direction to apply tension to the tether. In some embodiments, the tensioner includes a gauge ring disposed with the threaded cylindrical member. In some embodiments, the gauge ring is viewed through a window of a carriage that is disposed about the threaded cylindrical member. In some embodiments, visual indicia, including a plurality of markings are disposed adjacent to an edge or edges of the window. In some embodiments, the indicia lines include laser-marked lines. In some embodiments, a spring is disposed about the threaded cylindrical member. In some embodiments, the spring compresses once the tether is taut.

In some embodiments, the present surgical system includes a surgical tensioner which includes a pair of grasper prongs configured for gripping the tether. In some embodiments, the pair of grasper prongs are rounded and smooth to minimize damage to the tether when gripped.

In some embodiments, the present surgical system includes a surgical tensioner which includes a pair of grasper jaws and a counter torque mechanism including a shaft of a tensioner to apply a twisting tension to the tether. In some embodiments, the tensioner includes a ratchet configured to maintain tension of the tether. In some embodiments, the tensioner includes an indicator window defined from a surface of a carriage. In some embodiments, the tensioner includes a knob configured for rotation and translation relative to the carriage. In some embodiments, the knob is egg shaped. In some embodiments, the knob is engaged with a locking mechanism to operate the grasper jaws, for example, to orient the grasper jaws in an open position to capture the tether. In some embodiments, the knob is rotated in a direction to tension the tether. In some embodiments, a torsion spring begins to tension once the tether is taut and the torsion spring indicates tensioning of the tether. An inner link of the locking mechanism is viewed via the window and indicates tensioning relative to indicia, including laser-marked lines disposed about the window.

In some embodiments, the surgical tensioner described above is employed with a method that includes the step of inserting a tether through a thoracoscopic port. In some embodiments, the method includes the step of docking an end of the tensioner to a fixed angle screw disposed within a surgical site. In some embodiments, the method includes the step of loading the tether with the tensioner. In some embodiments, the knob is pushed in a forward direction to orient the grasper jaws into an open position to capture the tether. In some embodiments, the method includes the step of tensioning the tether, for example, the knob is rotated in a clockwise direction to rotate and tension the tether around the grasper jaws. In some embodiments, the method includes the step of indicating tether tensioning, for example, the torsion spring is viewed through the carriage window and does not compress until the tether is taut. In some embodiments, the method includes the step of securing the tether with one or more fixed angle screws, for example, a set screw is inserted into the shaft and is provisionally tightened with the fixed angle screw to fix the tether with the fixed angle screw. In some embodiments, the method includes the step of releasing the tether from the tensioner, for example, the knob is pushed in a direction to orient the grasper jaws into an open position to release or adjust the tether.

In some embodiments, the surgical system is used with surgical navigation, for example, fluoroscope or image guidance. In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-37, there are illustrated components of a surgical system, for example, a spinal correction system 10.

The components of spinal correction system 10 can be fabricated from biologically acceptable materials suitable for medical applications, including metals, synthetic polymers, ceramics and bone material and/or their composites. For example, the components of spinal correction system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 includes a surgical instrument, for example, a surgical tensioner 12. Surgical tensioner 12 is configured to engage one or more bone fasteners 14, including a fixed angle screw, and a longitudinal element, for example, a tether 16 to facilitate tension between the one or more bone fasteners 14 through a body cavity. Tensioner 12 extends between an end 18 and an end 20, as shown in FIG. 2. Tensioner 12 defines a longitudinal axis XX. In some embodiments, tensioner 12 may comprise overall and/or cross-section configurations, for example, cylindrical, round, oval, rectangular, polygonal, irregular, tapered, offset, staggered, uniform and non-uniform. In some embodiments, one or more of the surfaces of tensioner 12 may have alternate surface configurations, for example, rough, threaded for connection with surgical instruments, arcuate, undulating, porous, semi-porous, dimpled, polished and/or textured.

Tensioner 12 includes a member, for example, a shaft 22 as shown in FIG. 2. Shaft 22 extends between a proximal portion 24 and a distal portion 26. Distal portion 26 is configured to engage tether 16 and proximal portion 24 is configured to engage a body, for example, a carriage 28 that is engageable with tether 16 to fix tether 16 with carriage 28, as shown in FIG. 17. In some embodiments, shaft 22 may comprise overall and/or cross-section configurations, for example, cylindrical, round, oval, rectangular, polygonal, irregular, tapered, offset, staggered, uniform and non-uniform. In some embodiments, one or more of the surfaces of shaft 22 may have alternate surface configurations, for example, rough, threaded for connection with surgical instruments, arcuate, undulating, porous, semi-porous, dimpled, polished and/or textured.

Distal portion 26 includes a guide 30, as shown in FIGS. 2 and 3. Guide 30 includes an arcuate surface 32 and a transverse slot 34 configured to engage tether 16 to facilitate translation and/or tensioning of tether 16 relative to shaft 22. Guide 30 has a rotatable element, for example, a roller 36 that includes arcuate surface 32. Tether 16 frictionally engages roller 36 such that roller 36 rotates relative to shaft 22 to facilitate translation of tether 16 relative to shaft 22 during tensioning of tether 16. In some embodiments, tether 16 may slide along relative to arcuate surface 32, for example, surface 32 being fixed with distal portion 26. In some embodiments, tensioning of tether 16 can include increasing or decreasing tension of tether 16. In some embodiments, one or more of the surfaces of roller 36 may have alternate surface configurations, for example, undulating, porous, semi-porous, dimpled, polished and/or textured. In some embodiments, roller 36 may include one or more rollers 36. In some embodiments, the one or more rollers 36 can be the same or a different size. In some embodiments, roller 36 may be variously shaped, including, for example, spherical, cylindrical and/or tubular. In some embodiments, roller 36 may include one or more lubricating agents to facilitate translation of tether 16.

Transverse slot 34 is configured to orient, for example, guide tether 16 relative to vertebrae and is engageable with tether 16 to dispose tether 16 with one or more bone fasteners 14 disposed with the vertebrae, as shown in FIG. 17. In some embodiments, slot 34 may comprise various cross-section configurations, for example, cylindrical, round, oval, rectangular, polygonal, irregular, tapered, offset, staggered, uniform and non-uniform. In some embodiments, one or more of the surfaces of slot 34 may have alternate surface configurations, for example, rough, threaded for connection with surgical instruments, arcuate, undulating, porous, semi-porous, dimpled, polished and/or textured.

Figure 12:
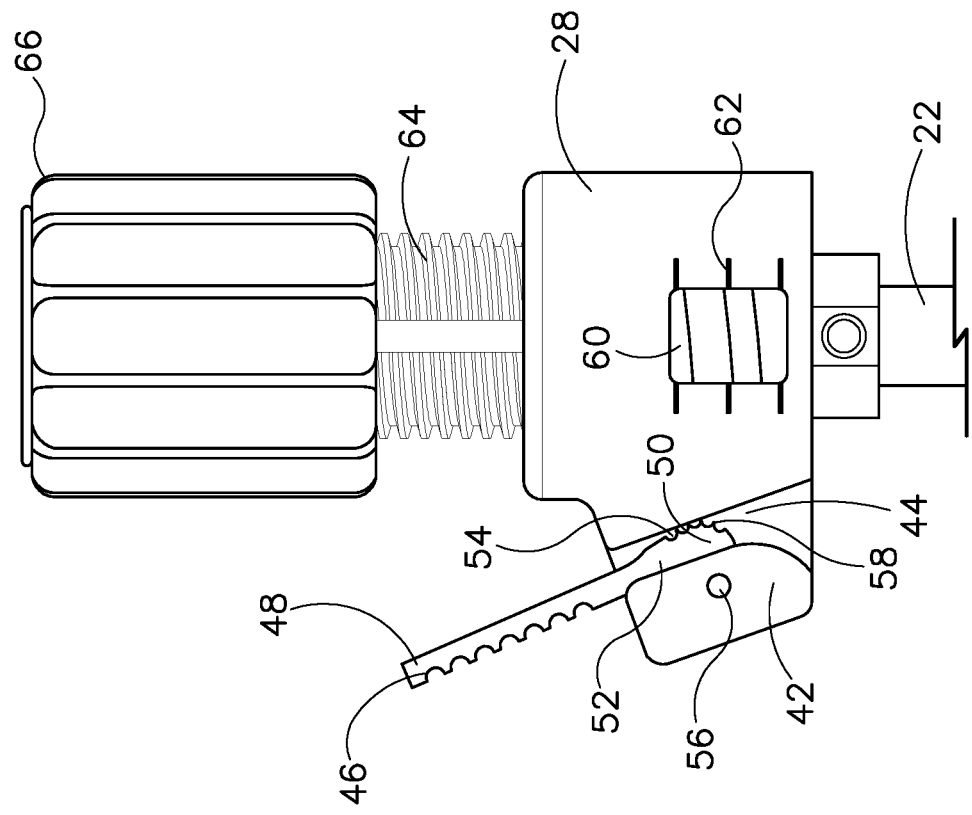
FIG. 12 is a break away view of components of the system shown in FIG. 1.
Figure 11:
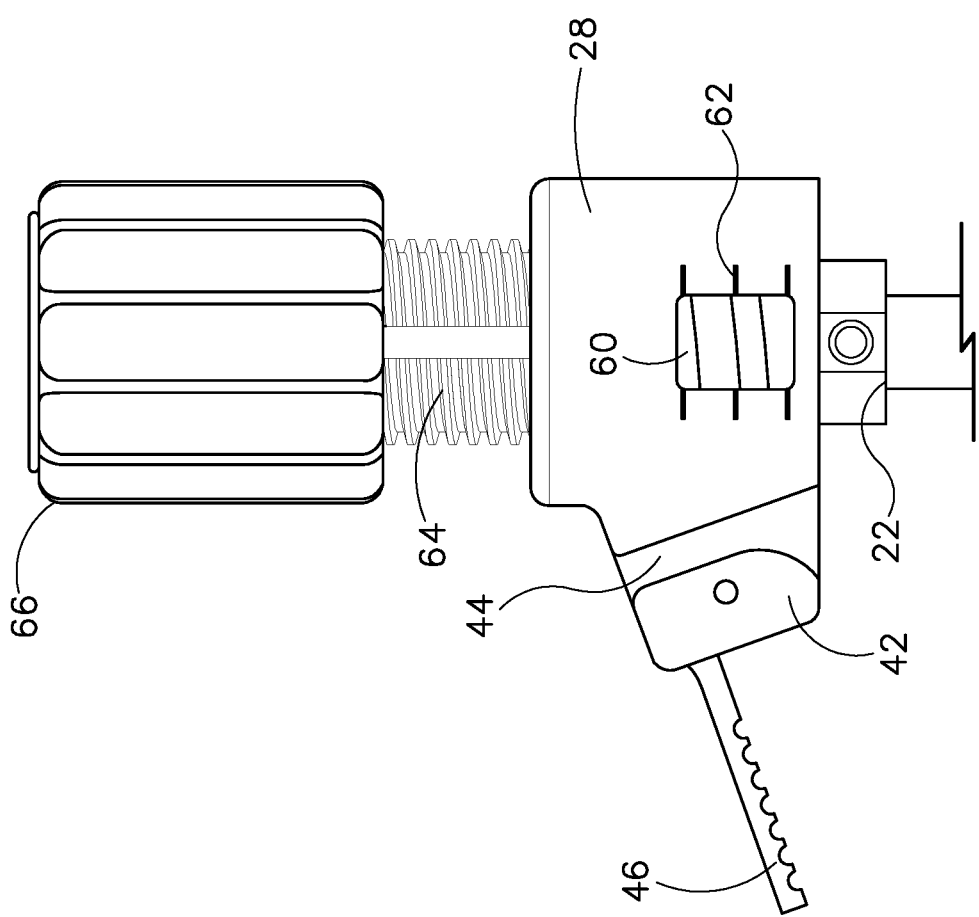
FIG. 11 is a break away view of components of the system shown in FIG. 1.

Carriage 28 extends between an end 38 and an end 40, as shown in FIG. 4. In some embodiments, carriage 28 may have various configurations, for example, circular, cylindrical, square, oval, rectangular, polygonal, irregular, tapered, offset, staggered and uniform. Carriage 28 includes a locking mechanism 42, as shown in FIGS. 4, 11 and 12. Locking mechanism 42 is configured to engage tether 16 to fix tether 16 with carriage 28. Locking mechanism 42 is disposed in a cavity 44 defined from a surface of carriage 28. Cavity 44 is configured to engage a portion of tether 16. In some embodiments, cavity 44 may have various cross sectional and/or axial configurations, for example, square, oval, rectangular, polygonal, irregular, offset, staggered, uniform and non-uniform.

Figure 14:
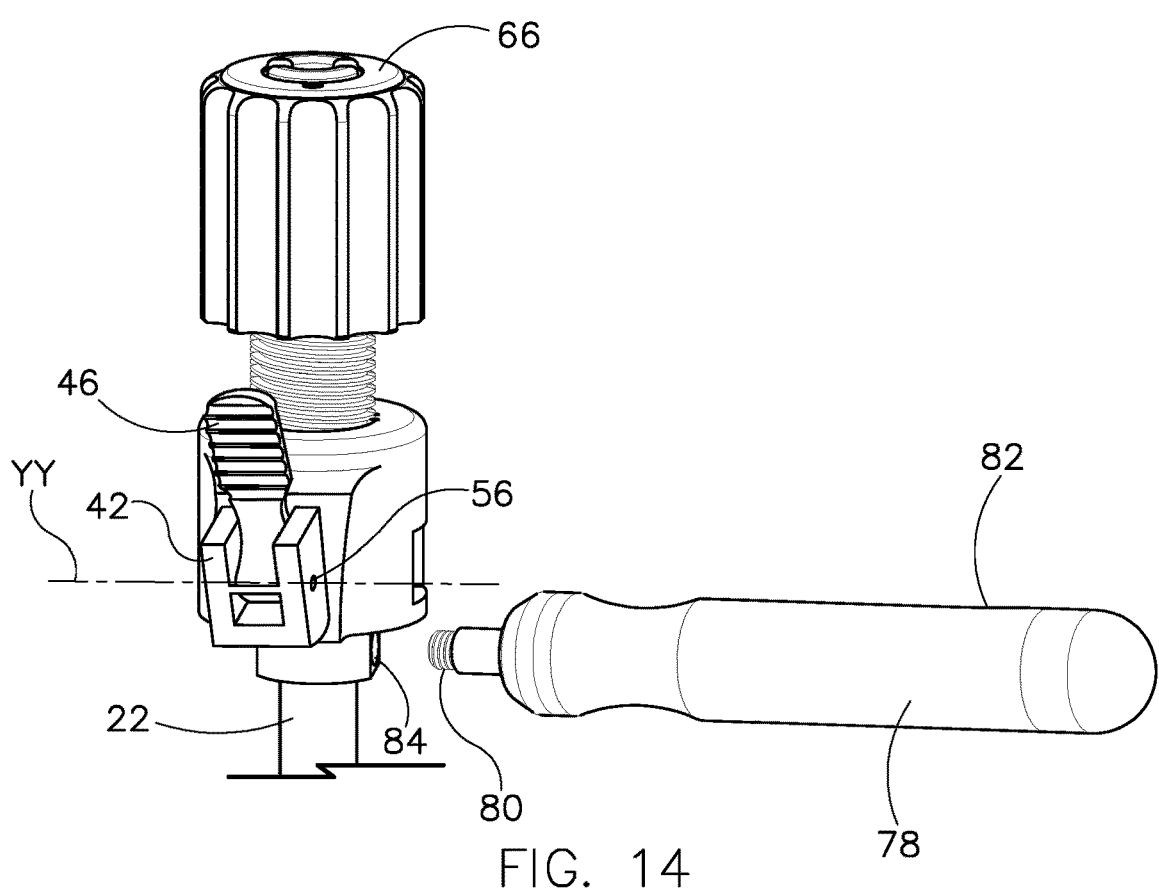
FIG. 14 is a break away view of components of the system shown in FIG. 9.
Figure 23:
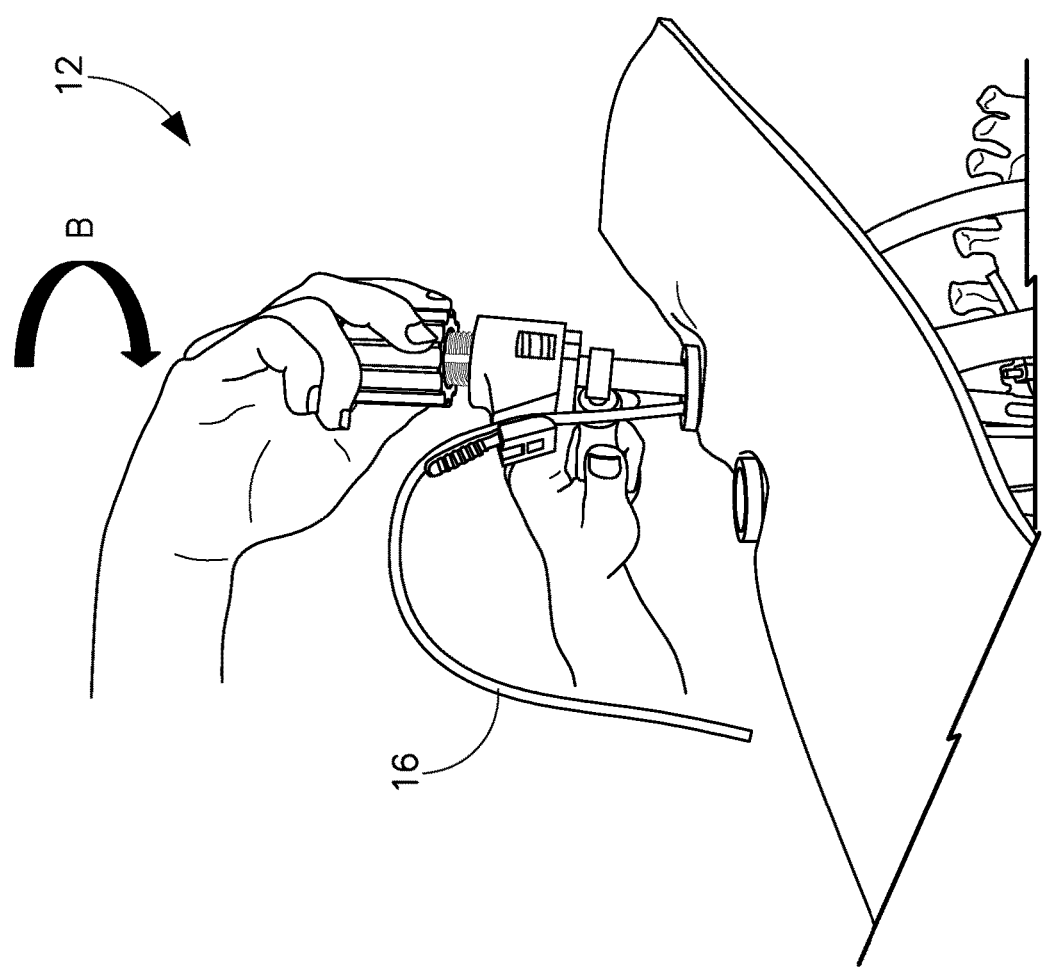
FIG. 23 is a perspective view of components of the system shown in FIG. 1 disposed with a patient body.

Locking mechanism 42 includes an arm, for example, a lever 46, as shown in FIGS. 11, 12 and 14. Lever 46 extends between an end 48 and an end 50, as shown in FIG. 12. End 48 is configured for engagement with a user. End 50 includes a cam 52, including a locking surface 54. Lever 46 is configured to pivot relative to an axis YY, as shown in FIG. 14, about a pin 56 disposed with a surface of carriage 28. Pin 56 is configured to facilitate engagement of locking surface 54 with tether 16. Locking surface 54 is disposed in cavity 44 such that locking surface 54 engages tether 16 to facilitate fixation of tether 16 with carriage 28 and to resist and/or prevent disengagement of tether 16 therefrom. In some embodiments, locking surface 54 is angled to facilitate disposal of tether 16 in a locked orientation, as described herein. In some embodiments, locking surface 54 may include penetrating members, for example, a plurality of teeth 58. In some embodiments, teeth 58 may have various configurations, for example, round, oval, rectangular, polygonal, irregular, tapered, offset, staggered, uniform and non-uniform.

Rotation of lever 46 causes locking surface 54 to pivot between a non-locked orientation and a locked orientation with tether 16, as shown in FIGS. 11 and 12. In the locked orientation, teeth 58 engage tether 16 to fix tether 16 with carriage 28. Locking surface 54 applies a compressive force and/or a friction force, as described herein, to fix tether 16 in the locked orientation. Locking surface 54 is configured to engage tether 16 to resist and/or prevent disengagement of tether 16 from cavity 44.

Figure 6:
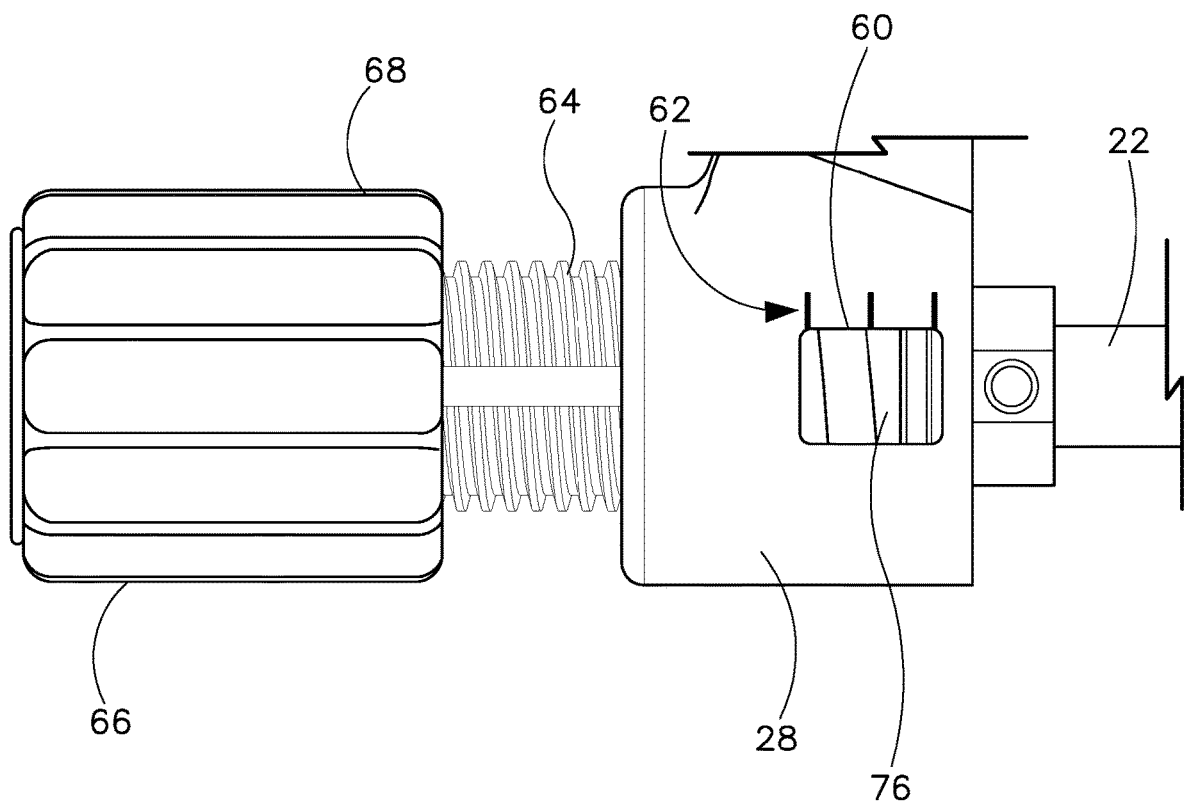
FIG. 6 is a break away view of components of the system shown in FIG. 1.
Figure 7:
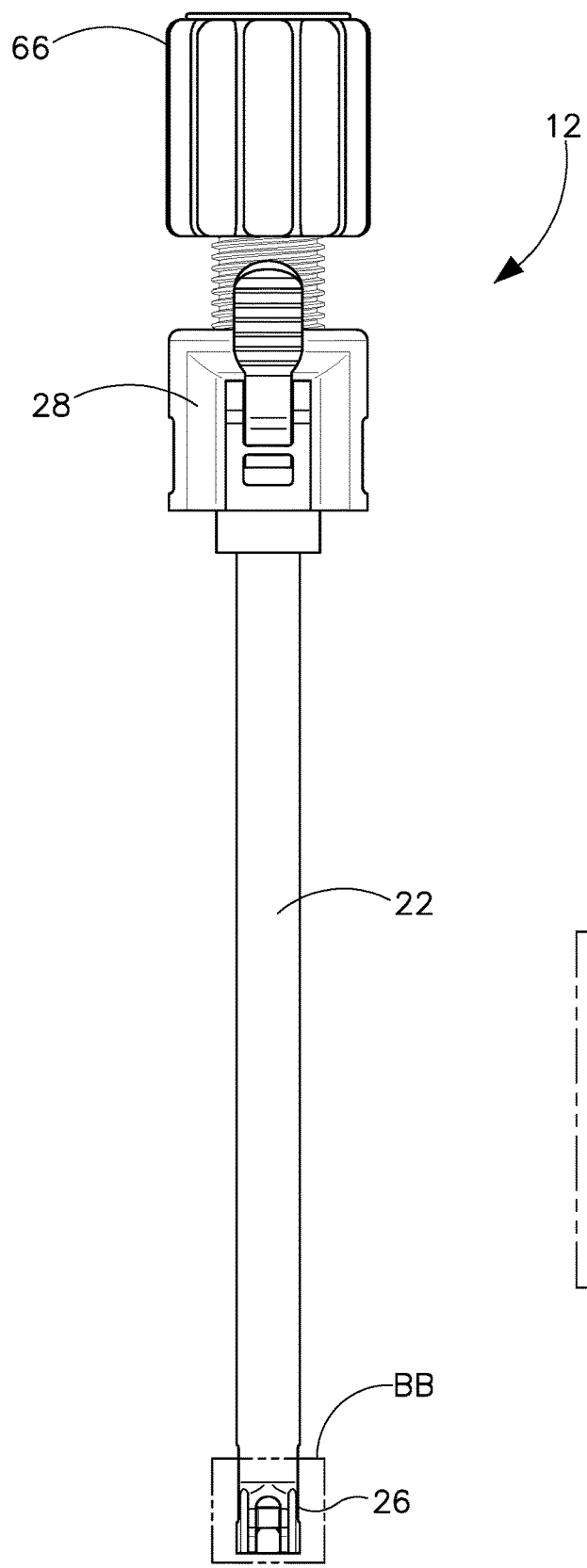
FIG. 7 is a side view of the components shown in FIG. 1.
Figure 8:
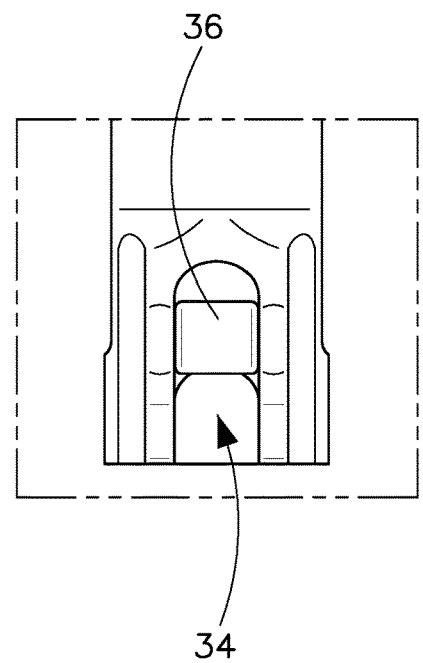
FIG. 8 is a break away view of detail BB in FIG. 7.
Figure 9:
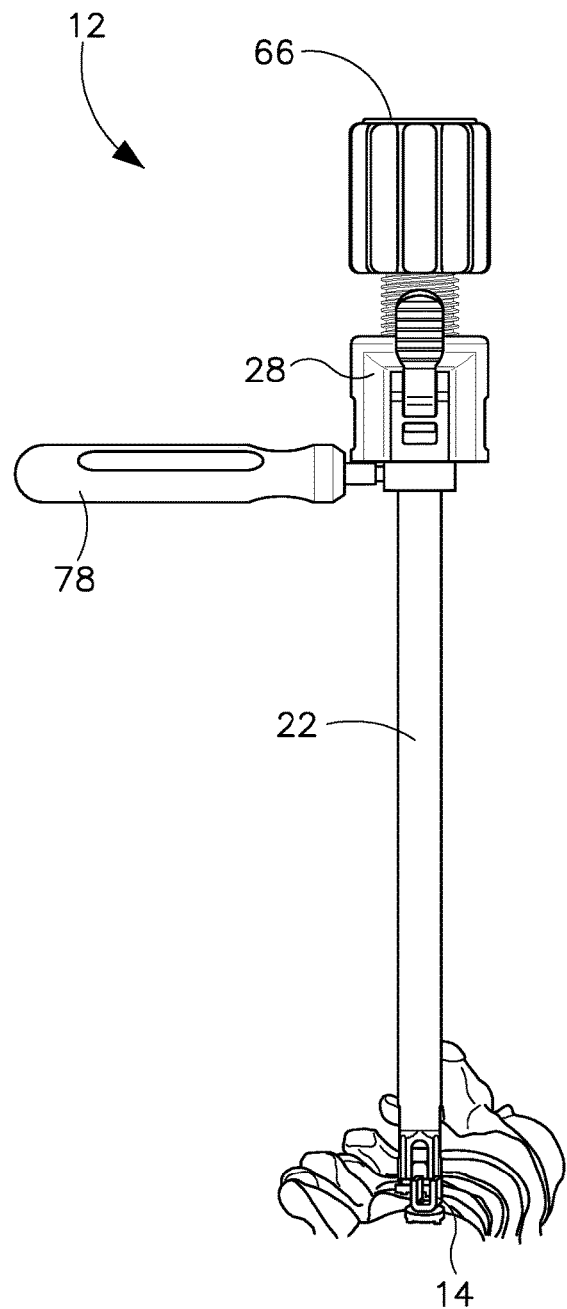
FIG. 9 is a perspective view of the components shown in FIG. 1 disposed with vertebrae.
Figure 10:
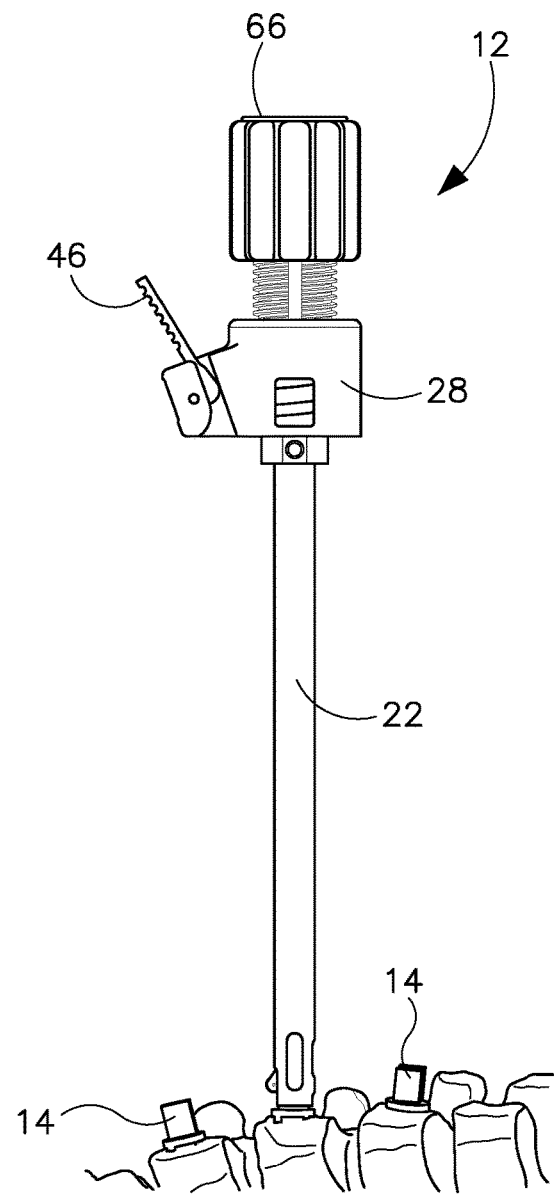
FIG. 10 is a side view of the components shown in FIG. 1 disposed with vertebrae.

Carriage 28 includes an outer surface that defines a transverse opening, for example, window 60, as shown in FIG. 6. Window 60 is configured to indicate tensioning of tether 16, as described herein. In some embodiments, window 60 can be variously shaped, including square, round, oval, rectangular, polygonal, irregular, tapered, offset, staggered, uniform and non-uniform. Carriage 28 includes a plurality of graduations 62 disposed on the outer surface and adjacent window 60. Plurality of graduations 62 are configured to indicate translation of a threaded cylindrical member 64 disposed within carriage 28 relative to shaft 22 that translates during tensioning of tether 16, as described herein. In some embodiments, plurality of graduations 62 include laser marked lines. In some embodiments, plurality of graduations 62 provide reference of dimension, including length, depth and/or height.

Figure 5:
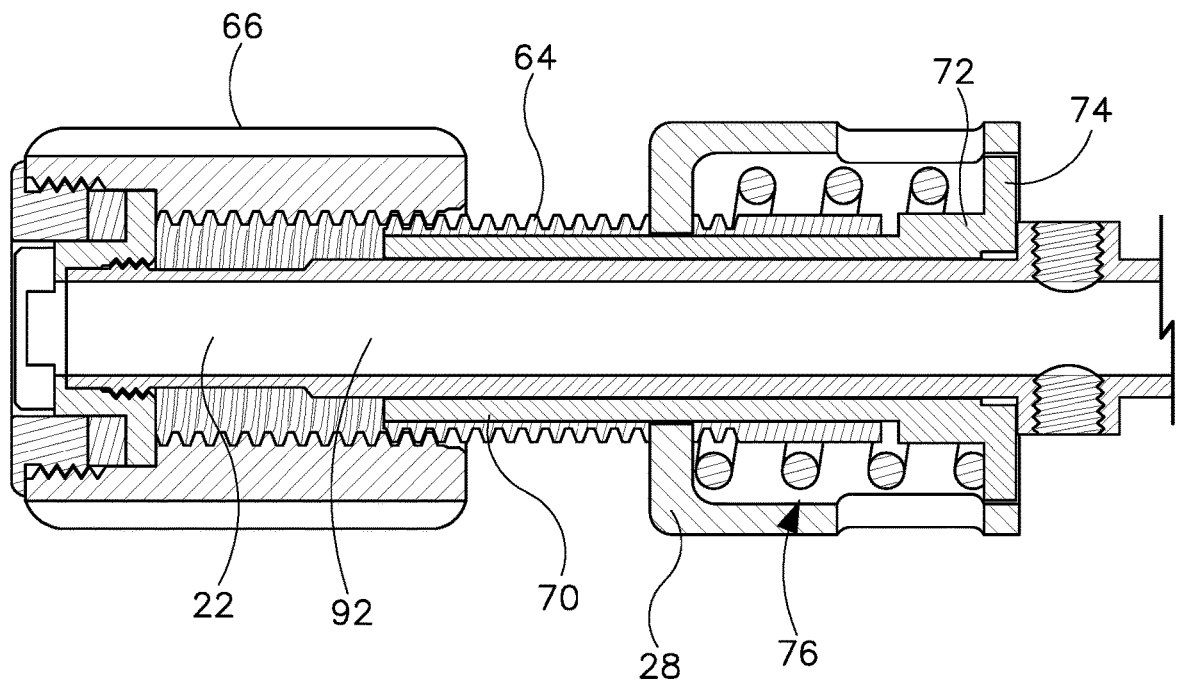
FIG. 5 is a break away cross sectional view of components of the system shown in FIG. 1.

Tensioner 12 includes an actuator, for example, a knob 66 that is connected with shaft 22 and threaded cylindrical member 64, as shown in FIGS. 5 and 6, to incrementally tension tether 16. Knob 66 is rotatable relative to axis XX to incrementally tension tether 16, as shown in FIG. 2. Knob 66 is threadingly engaged with threaded cylindrical member 64 such that rotation of knob 66 causes translation of carriage 28 relative to shaft 22. Knob 66 includes a surface 68 configured to facilitate gripping and rotation of knob 66 by a user, as shown in FIG. 6. In some embodiments, surface 68 may have alternate surface configurations, for example, grooved, rough, threaded for connection with surgical instruments, arcuate, undulating, porous, semi-porous, dimpled, polished and/or textured.

As described above, threaded cylindrical member 64 is threadingly engaged with knob 66 and is translatable within carriage 28. In some embodiments, threaded cylindrical member 64 includes a base. Threaded cylindrical member 64 includes an end 70 and an end 72, as shown in FIG. 5. End 70 is configured to engage knob 66 and end 72 is configured to engage an interior of carriage 28. End 72 includes a flange 74. Flange 74 is configured to engage a biasing member, for example, a spring 76, as shown in FIG. 5, to facilitate or indicate tensioning of tether 16. Threaded cylindrical member 64 including flange 74 is rotated in a direction to translate flange 74 to tension tether 16. In some embodiments, flange 74 includes various cross-section configurations, for example, cylindrical, round, oval, rectangular, polygonal, irregular, tapered, offset, staggered, uniform and non-uniform. In some embodiments, one or more of the surfaces of flange 74 may have alternate surface configurations, for example, rough, arcuate, undulating, porous, semi-porous, dimpled, polished and/or textured.

Spring 76 is disposed about a portion of threaded cylindrical member 64 and is disposed within carriage 28, as shown in FIGS. 5 and 6. Spring 76 is movable within carriage 28 for tensioning tether 16. Spring 76 is movable in an expanded or a contracted orientation. In the expanded orientation, spring 76 coupled with flange 74 is configured to facilitate tensioning of tether 16. Spring 76 is configured to contract once slack is removed from tether 16 and the contraction of spring 76 facilitates translation of flange 74 relative to window 60 and plurality of graduations 62. Spring 76 is viewed through window 60 and plurality of graduations 62 enable a user to determine the amount of tension applied to tether 16 relative to a starting point of carriage 28 on shaft 22.

Figure 13:
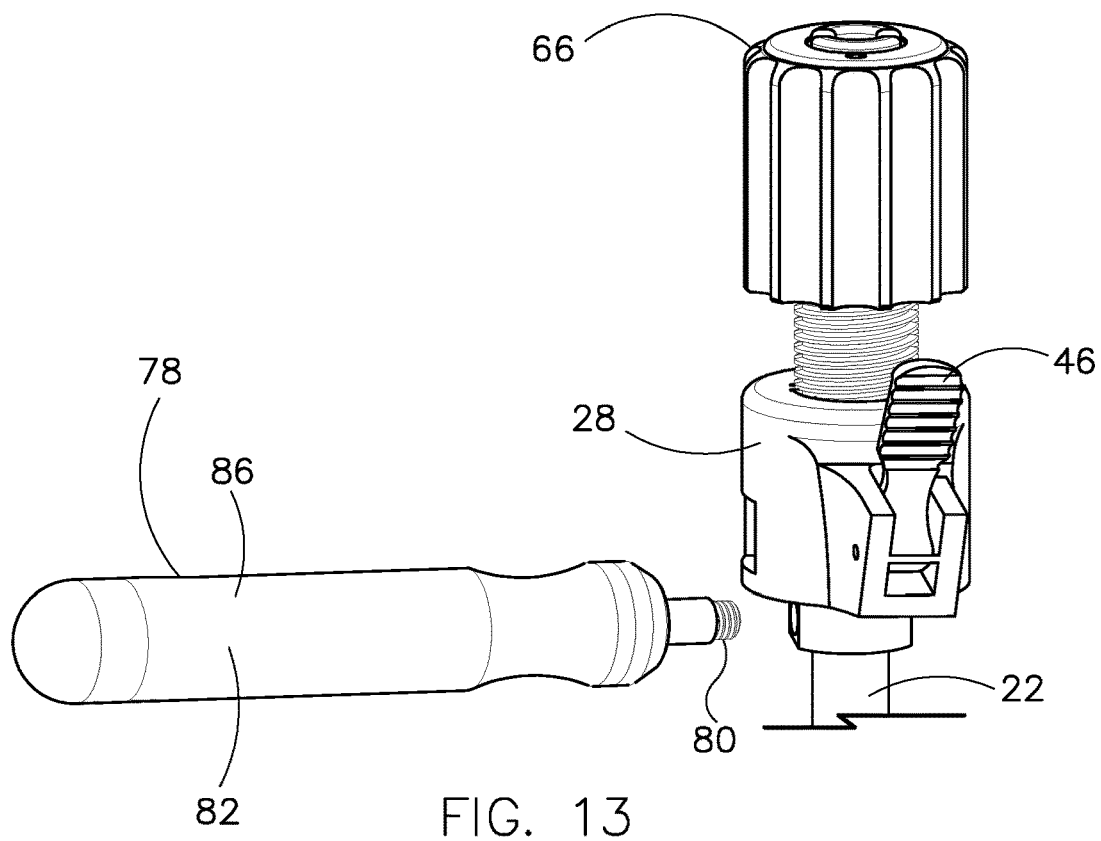
FIG. 13 is a break away view of components of the system shown in FIG. 9.

Tensioner 12 includes a handle 78, as shown in FIGS. 13 and 14. Handle 78 extends between an end 80 and an end 82. End 80 is configured for threaded engagement with a threaded opening 84 defined from a surface of shaft 22. Opening 84 is disposed transverse relative to axis XX, as show in FIG. 14. In some embodiments, handle 78 is configured for use as a counter torque. In some embodiments, handle 78 is employed for one or more corrective maneuvers, including compression and/or derotation when employed with an additional counter torque component. In some embodiments, handle 78 is oriented in one or more orientations relative to shaft 22. In some embodiments, handle 78 is oriented in a side by side, irregular, uniform, non-uniform, offset and/or staggered orientation or arrangement relative to shaft 22. In some embodiments, handle 78 is a silicone handle.

Handle 78 includes a surface 86 configured to facilitate gripping. In some embodiments, surface 86 may have alternate surface configurations, for example, grooved, rough, threaded for connection with surgical instruments, arcuate, undulating, porous, semi-porous, dimpled, polished and/or textured.

Tether 16 includes a first end 87 and a second end 89, as shown in FIG. 16. In some embodiments, tether 16 includes a braided tether and is flexible. In some embodiments, spinal correction system 10 may include one or a plurality of tethers 16. In some embodiments, tether 16 has a flexible configuration and may be fabricated from materials, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In some embodiments, tether 16 includes elastomeric properties for maintaining a selected load (e.g., force) over a selected distance. In some embodiments, tether 16 gradually achieves a correction or tensile load. In some embodiments, the flexibility of tether 16 includes movement in a lateral or side to side direction and prevents expanding and/or extension in an axial direction upon tensioning and attachment with a targeted portion of the anatomy. In some embodiments, all or only a portion of tether 16 may have a semi-rigid, rigid or elastic configuration, and/or have elastic properties, similar to the material examples described above, such that tether 16 provides a selective amount of expansion and/or extension in an axial direction. In some embodiments, tether 16 may be compressible in an axial direction. In some embodiments, tether 16 can include a plurality of separately attachable or connectable portions or sections, such as bands or loops, or may be monolithically formed as a single continuous element.

In some embodiments, tether 16 includes a uniform thickness/diameter. In some embodiments, tether 16 may have various surface configurations, for example, smooth and/or surface configurations to enhance fixation, for example, rough, arcuate, undulating, porous, semi-porous, dimpled, polished and/or textured. In some embodiments, the thickness defined by tether 16 may be uniformly increasing or decreasing, or have alternate diameter dimensions along its length. In some embodiments, tether 16 may have various cross section configurations, for example, oval, oblong, triangular, rectangular, square, polygonal, irregular, uniform, non-uniform, variable and/or tapered. In some embodiments, the surface of tether 16 may include engaging structures, for example, barbs, raised elements and/or spikes to facilitate engagement with tissue of the targeted anatomy.

In some embodiments, tether 16 may have various lengths. In some embodiments, tether 16 may be braided, such as a rope, or include a plurality elongated elements to provide a predetermined force resistance. In some embodiments, tether 16 may be made from autograft and/or allograft, and be configured for resorbable or degradable applications. In some embodiments, tether 16 is a cadaver tendon. In some embodiments, tether 16 is a tendon that may be harvested, for example, from a patient or donor. In some embodiments, a tendon harvested from a patient may be affixed in remote locations with the patient's body.

In assembly, operation and use, spinal correction system 10, similar to the systems and methods described herein, is employed with a surgical procedure, for example, a correction treatment of an affected portion of a spine, which may include a correction treatment to treat adolescent idiopathic scoliosis and/or other spinal deformities of a spine. In some embodiments, one (e.g., handle 78) of the components of spinal correction system 10 can be delivered or implanted as a pre-assembled device or can be assembled in situ. Spinal correction system 10 may be completely or partially revised, removed or replaced.

Figure 26:
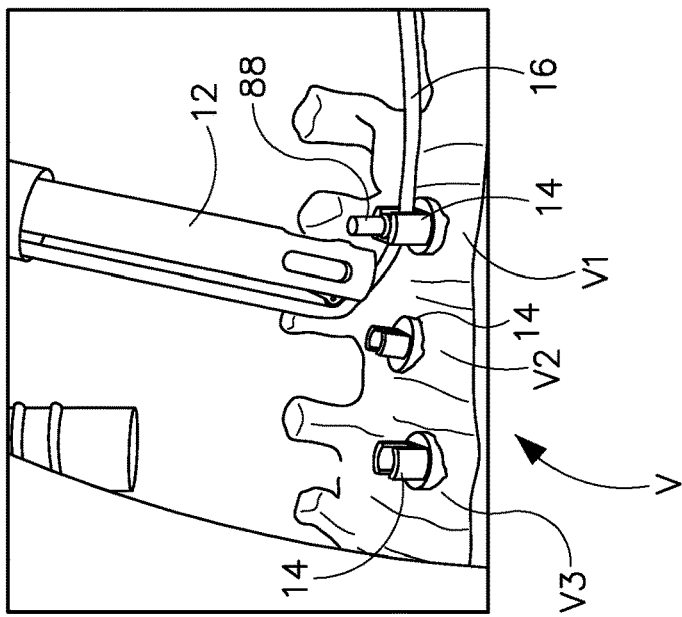
FIG. 26 is a break away view of components of the system shown in FIG. 1 disposed with a patient body.

In use, to treat a selected section of vertebrae V, as shown in FIG. 26, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway P, including a thoracoscopic port for implantation of components of spinal correction system 10. A preparation instrument (not shown) can be employed to prepare tissue surfaces of vertebrae V, as well as for aspiration and irrigation of a surgical region.

Figure 24:
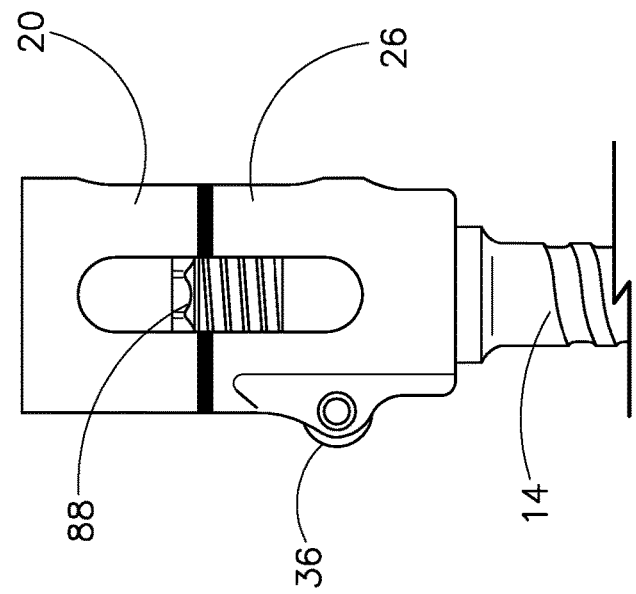
FIG. 24 is a break away view of components of the system shown in FIG. 1.

End 87 of tether 16 is grasped by a user, as shown in FIG. 16. A portion of tether 16 is oriented by the user to engage with slot 34 and roller 36, as shown in FIG. 15. The user grasps tether 16 in a taut configuration as a portion of tether 16 is aligned and disposed with cavity 44 of carriage 28, as shown in FIGS. 18-22. End 89 is grasped by the user, as shown in FIG. 16. Locking surface 54 is disposed in an open/non-locked orientation with tether 16 when a portion of tether 16 is disposed with cavity 44. Lever 46 is pivoted in a direction, for example, an upward direction as shown by arrow A in FIG. 16, to position locking surface 54 in a closed/locked orientation with tether 16 to secure tether 16 with tensioner 12, as shown in FIGS. 17, 21 and 22. Tensioner 12 is inserted into port P. End 20 of tensioner 12 along with a portion of tether 16 engages a bone fastener 14 fixed at a first vertebral level V1, as shown in FIGS. 24 and 26.

Figure 25:
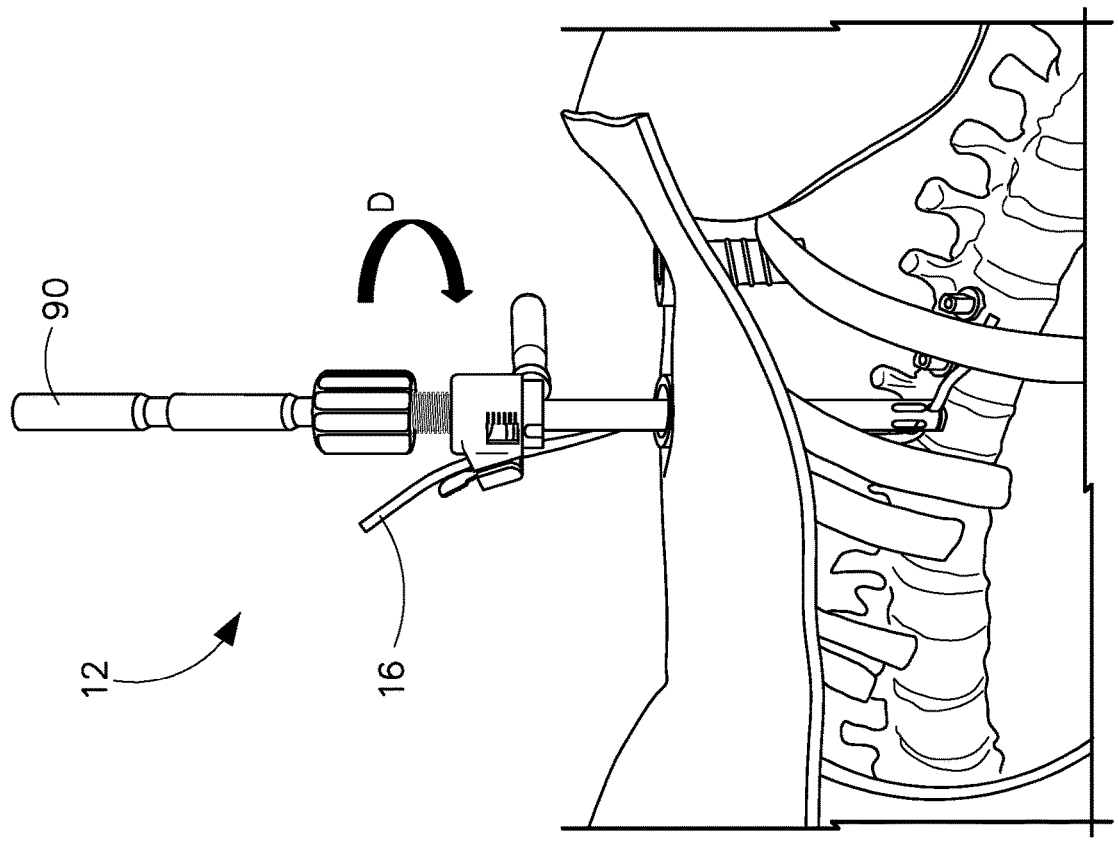
FIG. 25 is a perspective view of the components shown in FIG. 1 disposed with a patient body.

Knob 66 is placed in a first orientation by positioning knob 66 at end 70 of threaded cylindrical member 64, as shown in FIGS. 11, 12, 18 and 19. Knob 66 is rotated in a direction, for example, a clockwise direction, as shown by arrow B in FIG. 23. As knob 66 is rotated, knob 66 threadingly engages threaded cylindrical member 64 such that rotation of knob 66 causes translation of threaded cylindrical member 64 and carriage 28 in a direction, for example, an upward direction, as shown by arrow C in FIG. 17 relative to shaft 22. Spring 76 is compressed/contracted during translation of carriage 28 via flange 74 and is viewable through window 60. Translation of carriage 28 in an upward direction causes tether 16 to tension. During carriage 28 translation, exterior surfaces of tether 16 engage roller 36 to facilitate translation of tether 16 relative to shaft 22 during tensioning, as shown in FIG. 3. Tether 16 is fixed with bone fastener 14 via a set screw 88, as shown in FIG. 26. A driver 90 is disposed through a channel 92 of shaft 22 and engages with set screw 88, as shown in FIGS. 5 and 25. Driver 90 is rotated in a direction, for example, a clockwise direction, as shown by arrow D in FIG. 25 to tighten set screw 88 with bone fastener 14. Driver 90 is removed from channel 92 of shaft 22.

Figure 28:
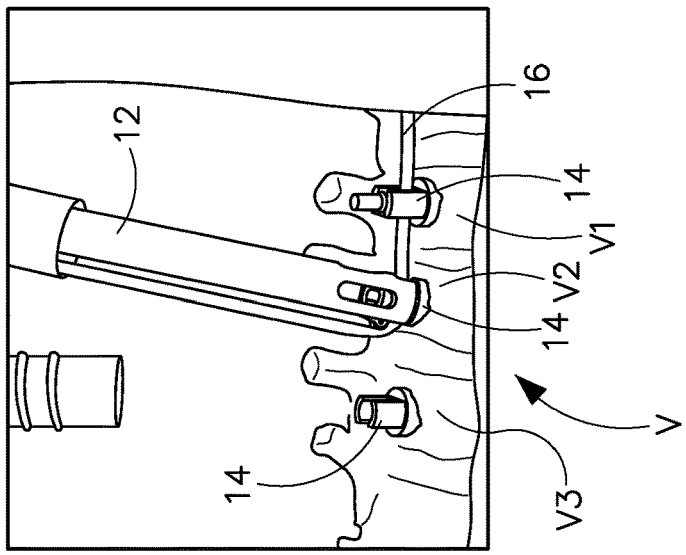
FIG. 28 is a break away view of components of the system shown in FIG. 1 disposed with a patient body.
Figure 27:
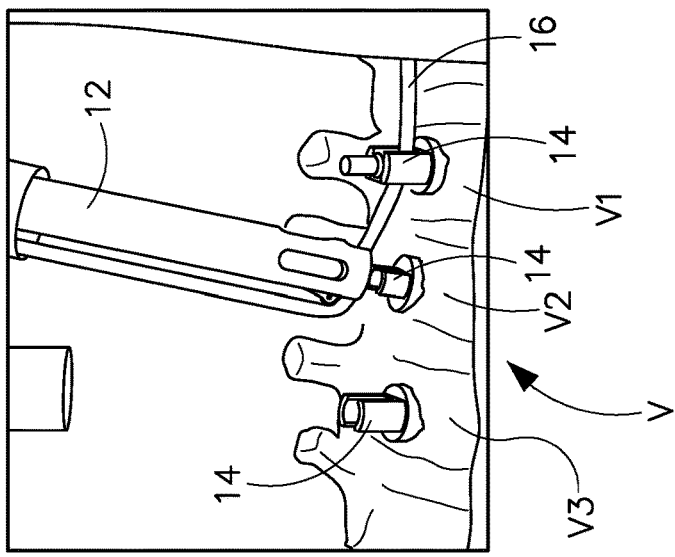
FIG. 27 is a break away view of components of the system shown in FIG. 1 disposed with a patient body.
Figure 29:
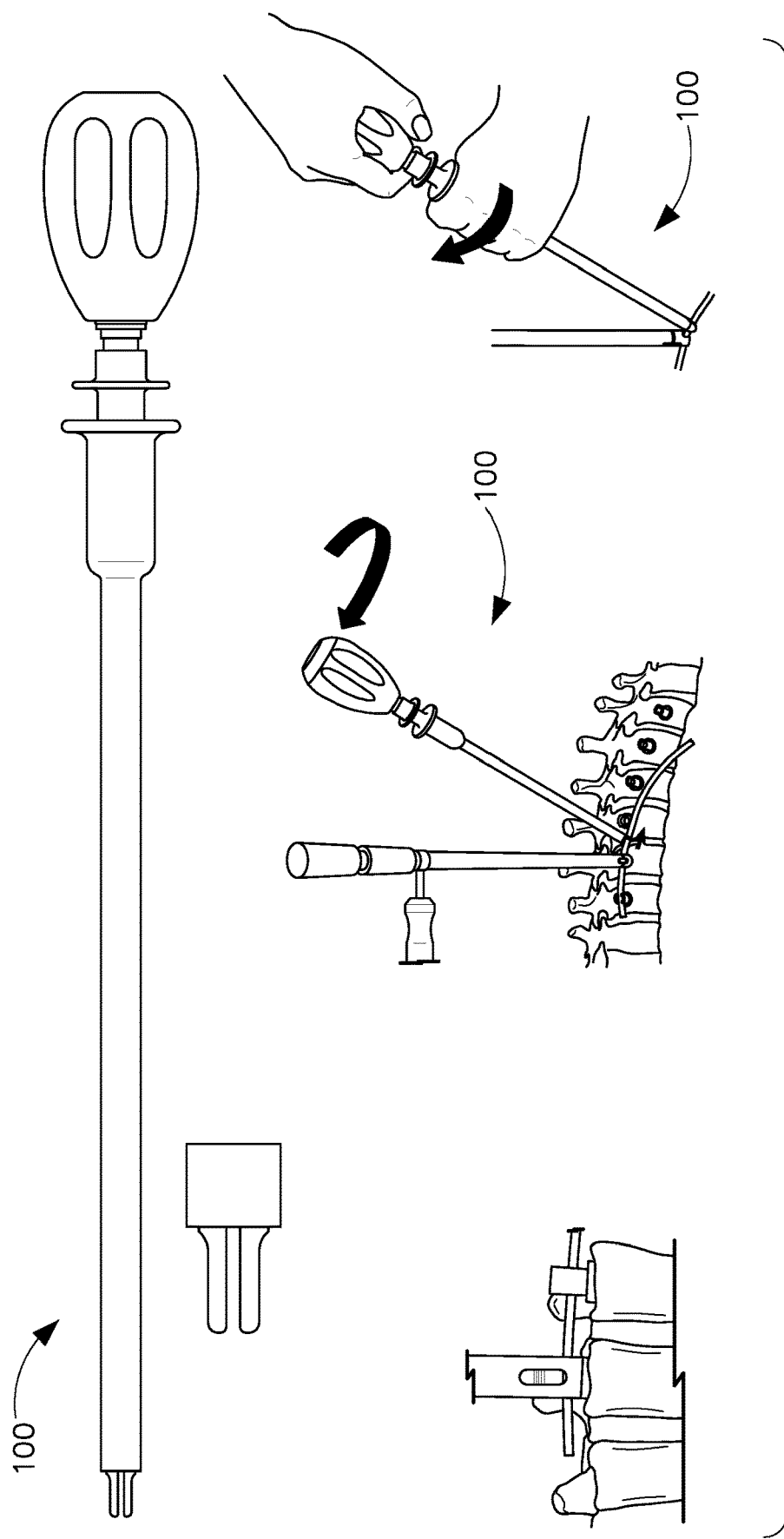
FIG. 29 is a perspective view of one embodiment of components of a surgical system in accordance with the principles of the present disclosure.
Figure 36:
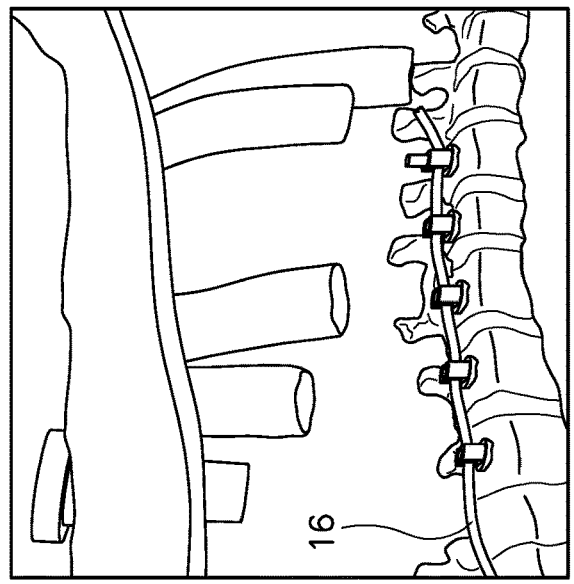
FIG. 36 is a perspective view of components of the system shown in FIG. 1 disposed with a patient body.
Figure 35:
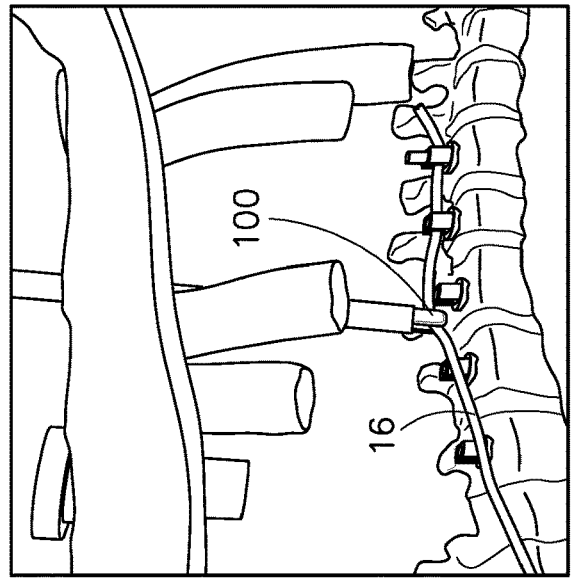
FIG. 35 is a perspective view of components of the system shown in FIG. 1 disposed with a patient body.
Figure 34:
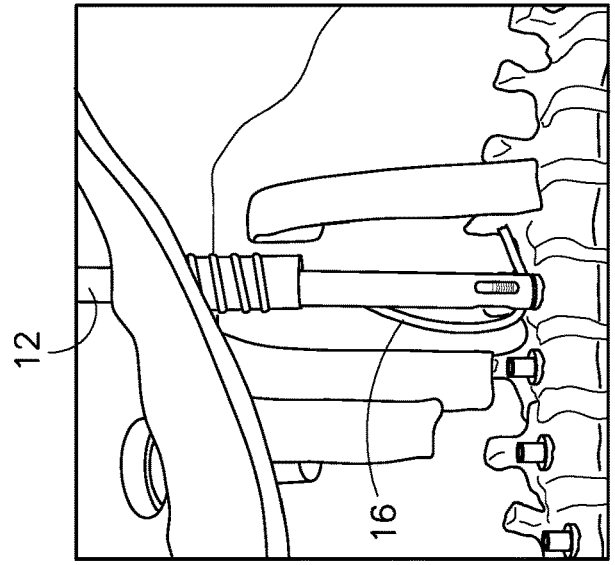
FIG. 34 is a perspective view of components of the system shown in FIG. 1 disposed with a patient body.
Figure 37:
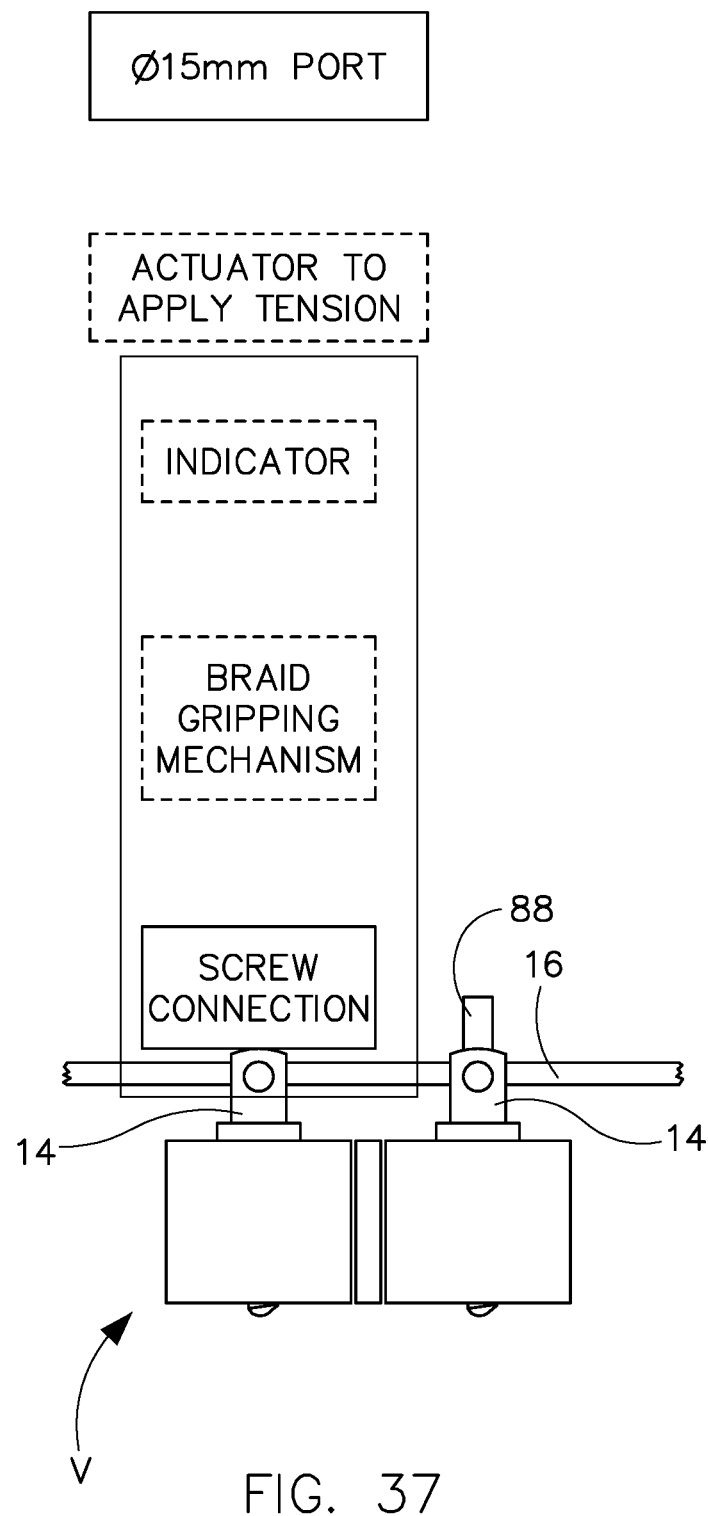
FIG. 37 is a side view of one embodiment of components of a surgical system in accordance with the principles of the present disclosure disposed with vertebrae.

Tensioner 12 is translated to a second bone fastener 14 fixed at a second vertebral level V2, as shown in FIG. 26. In some embodiments, the same port P is employed to insert tensioner 12 into the surgical site. In some embodiments, a different port P is employed to insert tensioner 12 into the surgical site. The user grips end 89 of tether 16 while slot 34 of tensioner 12 translates tether 16 to second bone fastener 14, as shown in FIGS. 26-28. In some embodiments, a grasping tool 100, as shown in FIGS. 29 and 35 is configured for disposal with shaft 22 of tensioner 12 to translate tether 16 to second bone fastener 14. Tensioner 12 along with a portion of tether 16 engages with second bone fastener 14, as shown in FIGS. 27 and 28. Tether 16 is tensioned and driver 90 tightens a second set screw 88 with second bone fastener 14 in the manner described above with regard to first bone fastener 14. Tensioner 12 is translated to a third bone fastener 14 fixed at a third vertebral level V3, as shown in FIG. 28 in the manner described above with regard to second bone fastener 14. Tether 16 is tensioned between first bone fastener 14 and second bone fastener 14, and driver 90 tightens a third set screw 88 with third bone fastener 14 in the manner described above. In some embodiments, a plurality of bone fasteners 14 are fixed with tether 16, as shown in FIGS. 34-36.

To release tether 16 from tensioner 12, knob 66 is rotated in a direction, for example, a counterclockwise direction, as shown by arrow E in FIG. 31. As knob 66 is rotated, knob 66 threadingly engages with threaded cylindrical member 64 such that rotation of knob 66 causes translation of threaded cylindrical member 64 and carriage 28 in a direction, for example, a downward direction, as shown by arrow F in FIG. 31 relative to shaft 22. Lever 46 is pivoted in a direction, for example, a downward direction as shown by arrow G in FIG. 32, to dispose locking surface 54 in an open/non-locked orientation to release tether 16.

In some embodiments, one or all of the components of spinal correction system 10 can be delivered or implanted as a pre-assembled device or can be assembled in situ, in a selected order of assembly or the order of assembly of the particular components of system 10 can be varied according to practitioner preference, patient anatomy or surgical procedure parameters. Spinal implant system 10 may be completely or partially revised, removed or replaced.

Upon completion of the procedure, the surgical instruments, assemblies and non-implanted components of spinal correction system 10 are removed from the surgical site and the incision is closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10.

In some embodiments, spinal correction system 10 includes an agent, which may be disposed, packed, coated or layered within, on or about the components and/or surfaces of spinal correction system 10. In some embodiments, the agent may include one or a plurality of therapeutic agents and/or pharmacological agents for release, including sustained release, to treat, for example, pain, inflammation and degeneration.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 may be used to prevent or minimize curve progression in individuals of various ages.

Figure 38:
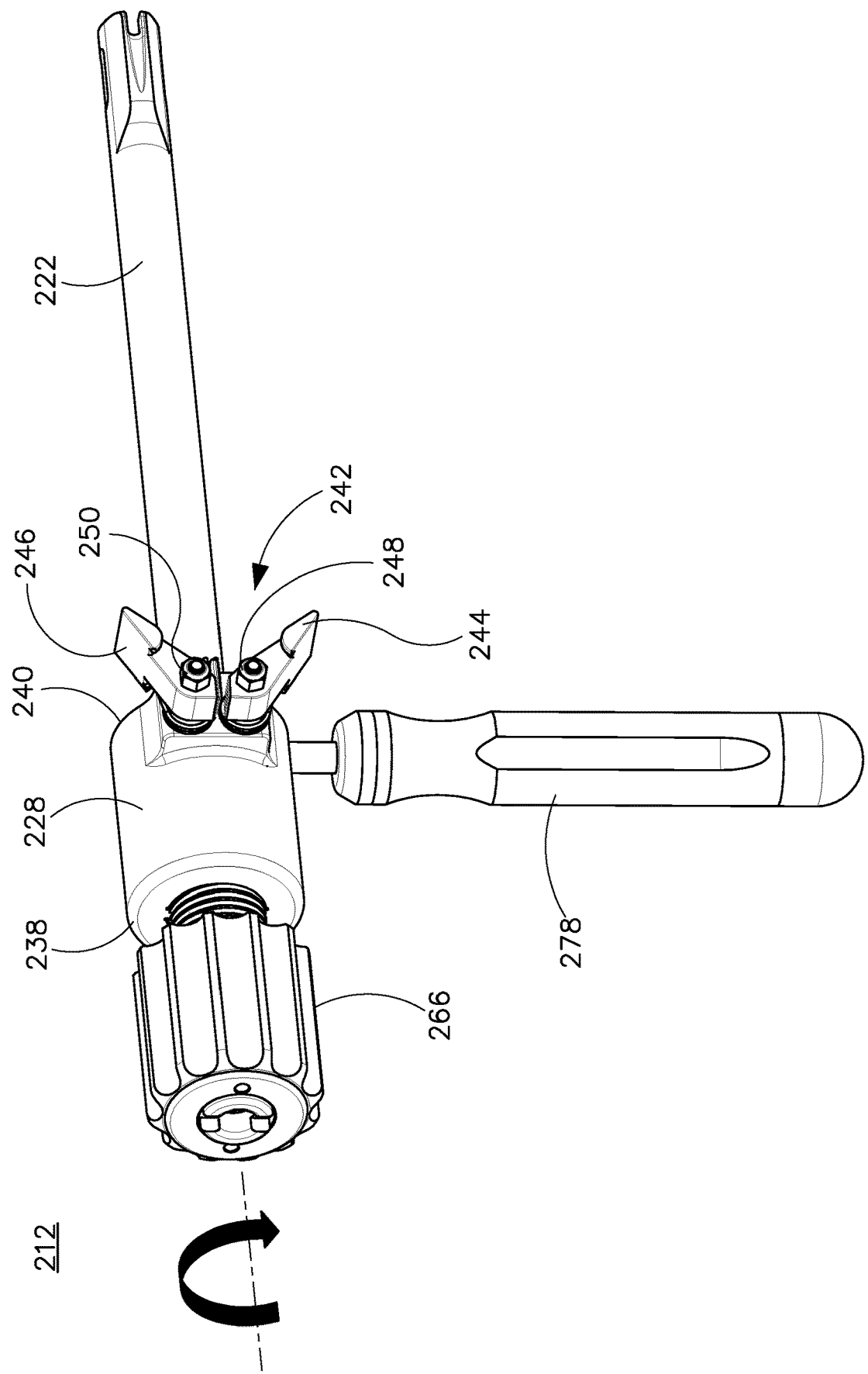
FIG. 38 is a perspective view of one embodiment of components of a surgical system in accordance with the principles of the present disclosure.

In one embodiment, as shown in FIG. 38-43, spinal correction system 10, similar to the systems and methods described above with regard to FIGS. 1-37, includes a tensioner 212, similar to tensioner 12 described herein. Tensioner 212 includes a shaft 222, a threaded cylindrical member 264, a knob 266, a spring 276 and a handle 278, similar to shaft 22, threaded cylindrical member 64, knob 66, spring 76 and handle 78 described above with regard to tensioner 12. Tensioner 212 includes a carriage 228, similar to carriage 28 described herein. Carriage 228 extends between an end 238 and an end 240, as shown in FIG. 38. In some embodiments, carriage 228 may have various configurations, for example, circular, cylindrical, square, oval, rectangular, polygonal, irregular, tapered, offset, staggered and uniform. Carriage 228 includes a locking mechanism 242, as shown in FIG. 38. Locking mechanism 242 is configured to engage with tether 16 to fix tether 16 with carriage 228.

Figure 43:
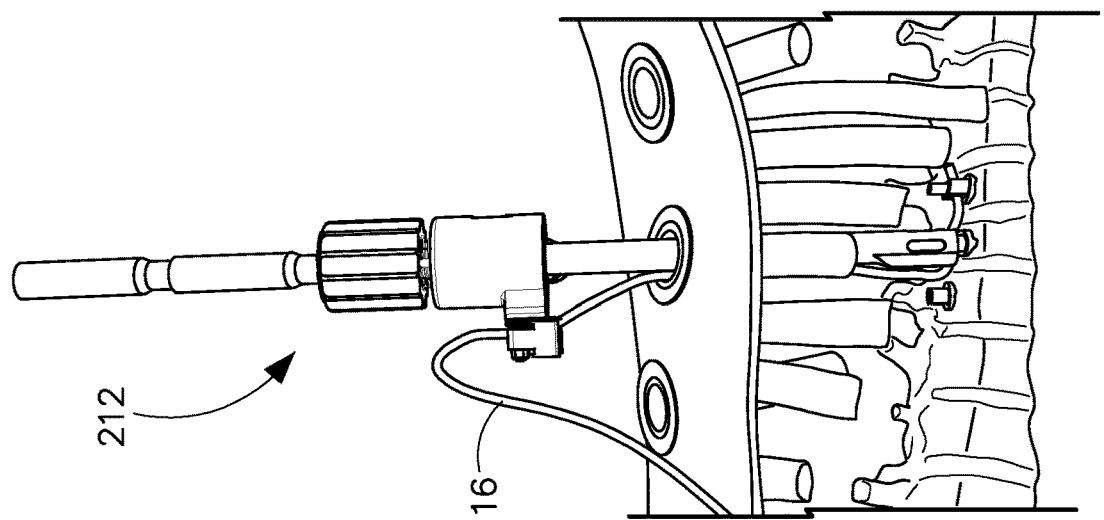
FIG. 43 is a perspective view of the components shown in FIG. 38 disposed with a patient body.
Figure 42:
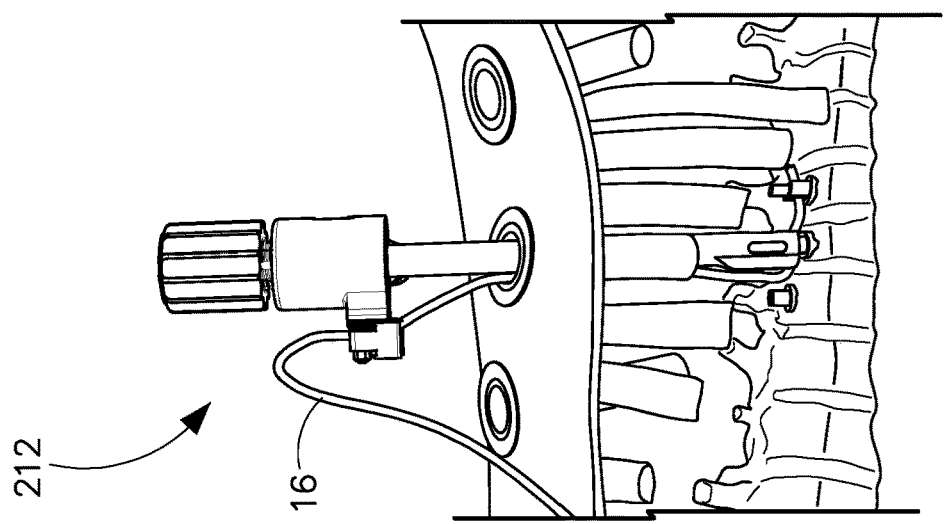
FIG. 42 is a perspective view of the components shown in FIG. 38 disposed with a patient body.
Figure 41:
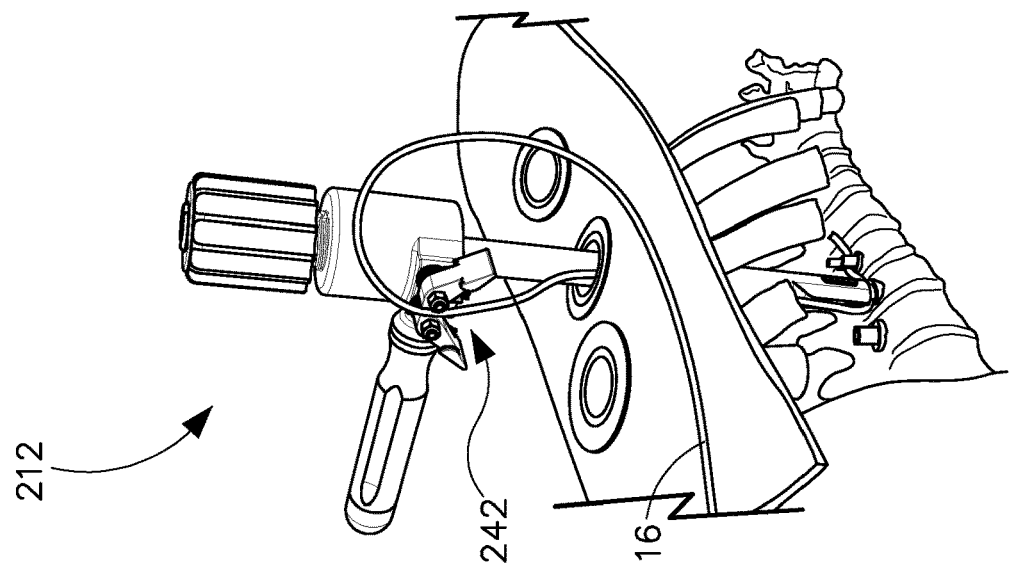
FIG. 41 is a perspective view of the components shown in FIG. 38 disposed with a patient body.

Locking mechanism 242 includes a lever 244 and a lever 246, as shown in FIG. 38. Levers 244, 246 are configured to engage a portion of tether 16. Lever 244 includes a spring loaded cam 248 and lever 246 includes a spring loaded cam 250. Rotation of levers 244, 246 causes levers 244, 246 to pivot between a non-locked orientation and a locked orientation with tether 16, as shown in FIGS. 38 and 41. In the locked orientation, levers 244, 246 engage tether 16 to fix tether 16 with carriage 228, as shown in FIG. 41. Locking mechanism 242 applies a compressive force and/or a friction force, as described herein, to fix tether 16 in the locked orientation. Locking mechanism 242 is configured to engage tether 16 to resist and/or prevent disengagement of tether 16 from levers 244, 246, as shown in FIGS. 41-43. In some embodiments, levers 244, 246 may include penetrating members, for example, a plurality of teeth (not shown) configured to assist in engagement of tether 16. In some embodiments, levers 244, 246 may have various configurations, for example, round, oval, rectangular, polygonal, irregular, tapered, offset, staggered, uniform and non-uniform.

Figure 39:
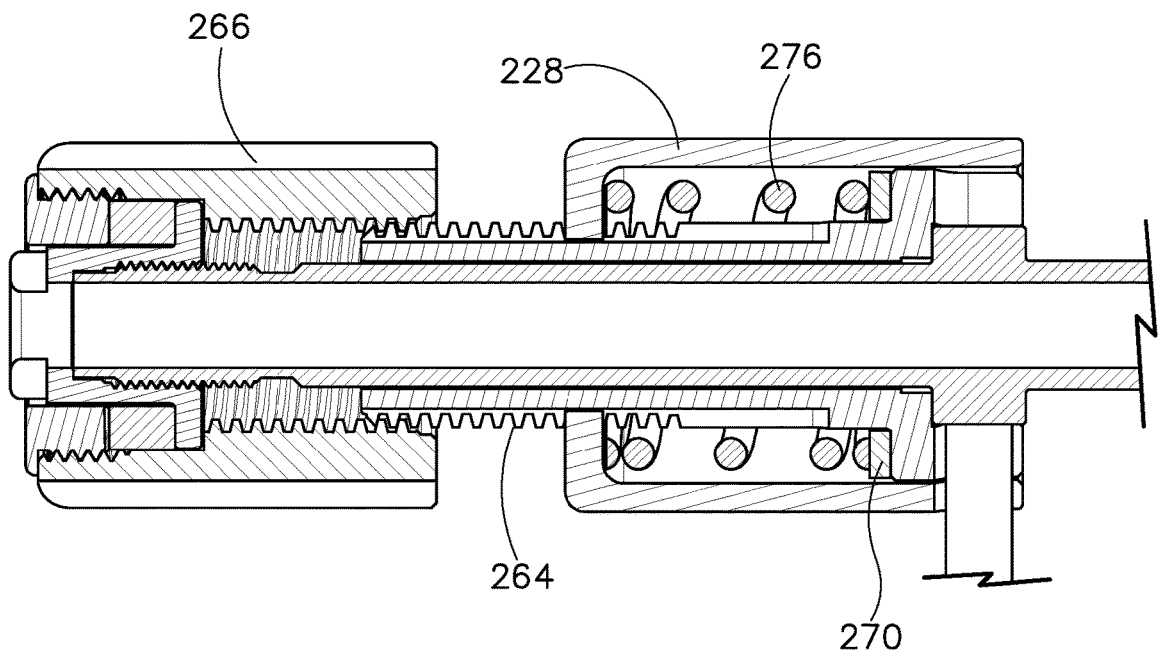
FIG. 39 is a cross sectional break away view of components of the system shown in FIG. 38.
Figure 40:
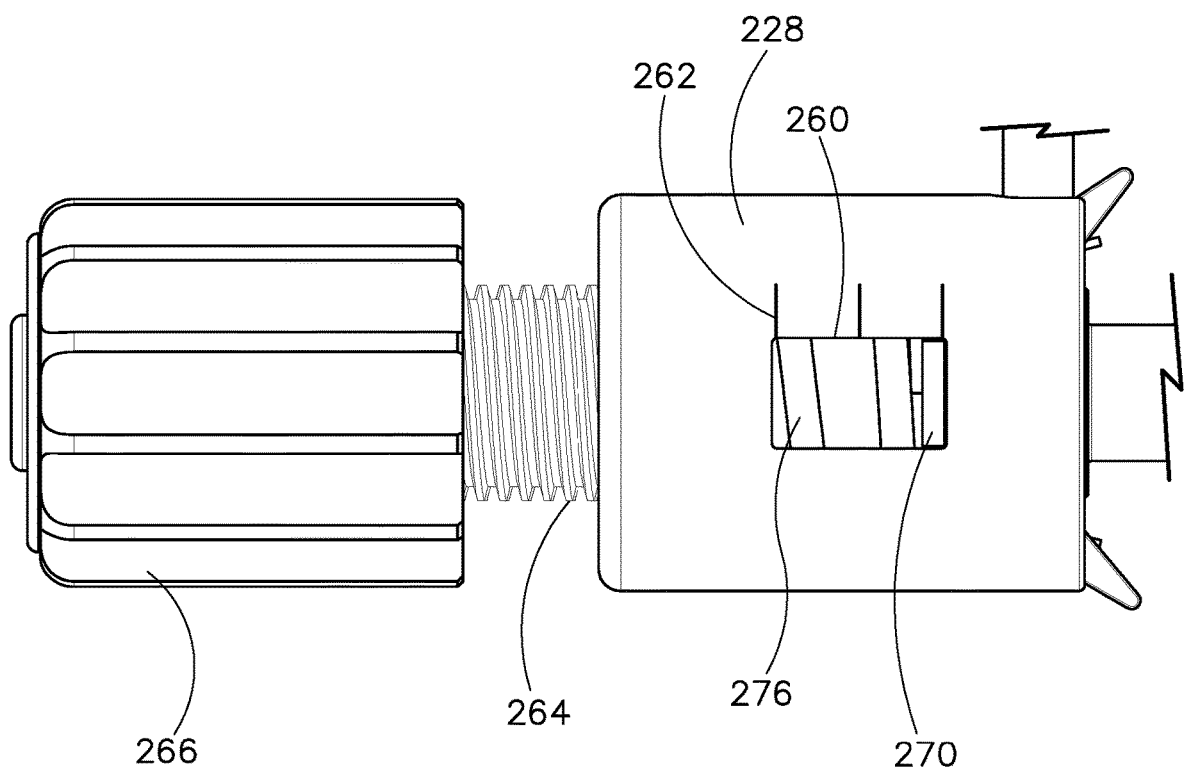
FIG. 40 is a break away view of components of the system shown in FIG. 38.

Carriage 228 includes an outer surface that defines a transverse opening, for example, a window 260 and a plurality of graduations 262 disposed on the outer surface and adjacent window 260, as shown in FIG. 40 and similar to window 60 and plurality of graduations 62, described above. Plurality of graduations 262 are configured to indicate translation of threaded cylindrical member 264 and a ring 270 disposed about threaded cylindrical member 264, as shown in FIGS. 39 and 40.

Figure 45:
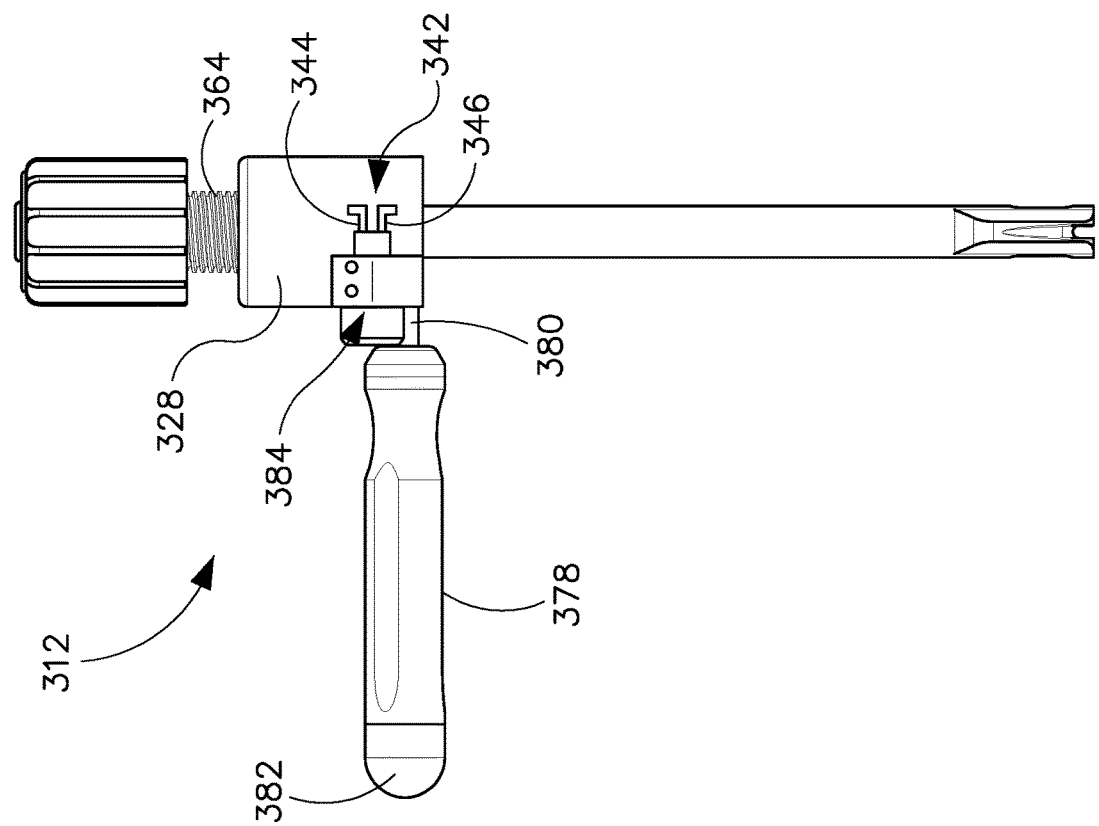
FIG. 45 is a perspective view of the components shown in FIG. 44.
Figure 44:
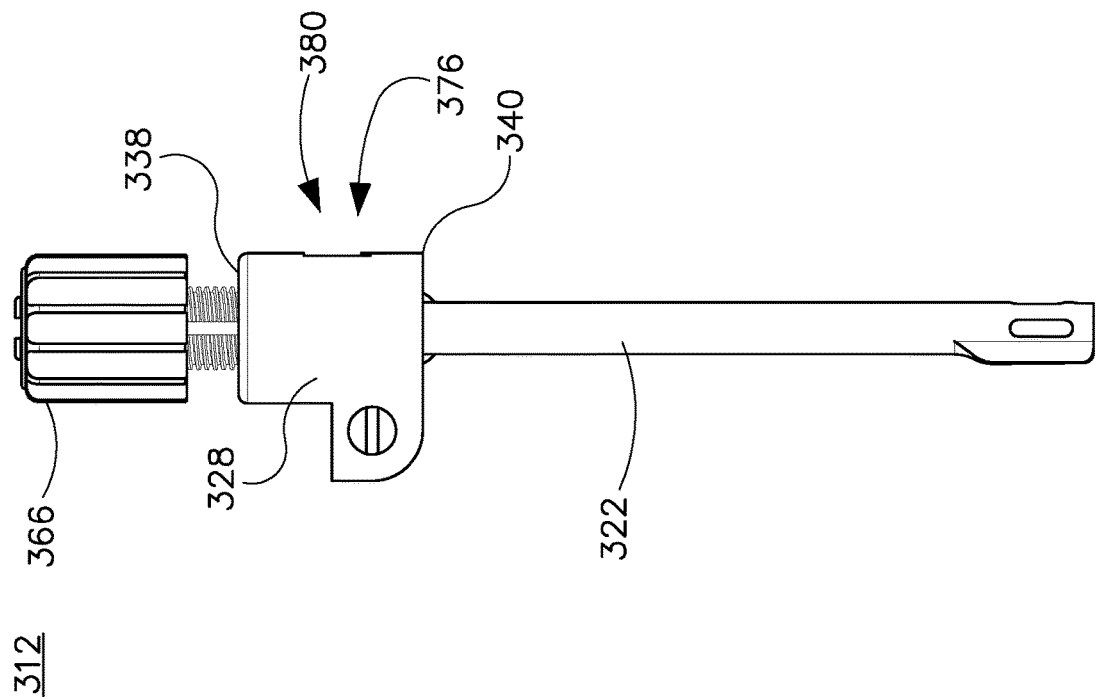
FIG. 44 is a side view of one embodiment of components of a surgical system in accordance with the principles of the present disclosure.

In one embodiment, as shown in FIGS. 44-45, spinal correction system 10, similar to the systems and methods described above with regard to FIGS. 38-43, includes a tensioner 312, similar to tensioner 212 described herein. Tensioner 312 includes a shaft 322, a threaded cylindrical member 364, a knob 366, a spring 376, a ring 380, and a handle 378, similar to shaft 222, threaded cylindrical member 264, knob 266, spring 276, ring 270 and handle 278 described above with regard to tensioner 212. Tensioner 312 includes a carriage 328, similar to carriage 228 described herein.

Carriage 328 extends between an end 338 and an end 340, as shown in FIG. 44. In some embodiments, carriage 328 may have various configurations, for example, circular, cylindrical, square, oval, rectangular, polygonal, irregular, tapered, offset, staggered and uniform. Carriage 328 includes a locking mechanism 342, as shown in FIG. 45. Locking mechanism 342 is configured to engage with tether 16 to fix tether 16 with carriage 328.

Locking mechanism 342 includes a grasper prong 344 and a grasper prong 346, as shown in FIG. 45. Grasper prongs 344, 346 are configured to engage a portion of tether 16. Locking mechanism 342 is configured to engage tether 16 to resist and/or prevent disengagement of tether 16 from grasper prongs 344, 346. In some embodiments, grasper prongs 344, 346 have a smooth surface configuration to reduce tether 16 damage during engagement with grasper prongs 344, 346. In some embodiments, grasper prongs 344, 346 may include penetrating members, for example, a plurality of teeth (not shown) configured to assist in engagement of tether 16. In some embodiments, grasper prongs 344, 346 may have various configurations, for example, round, oval, rectangular, polygonal, irregular, tapered, offset, staggered, uniform and non-uniform.

Handle 378 extends between an end 380 and an end 382, as shown in FIG. 45. End 380 is configured for engagement with an opening 384 defined from a surface of carriage 328. In some embodiments, handle 378 is oriented in one or more orientations relative to shaft 322. In some embodiments, handle 378 is oriented in a side by side, irregular, uniform, non-uniform, offset and/or staggered orientation or arrangement relative to shaft 322.

Figure 46:
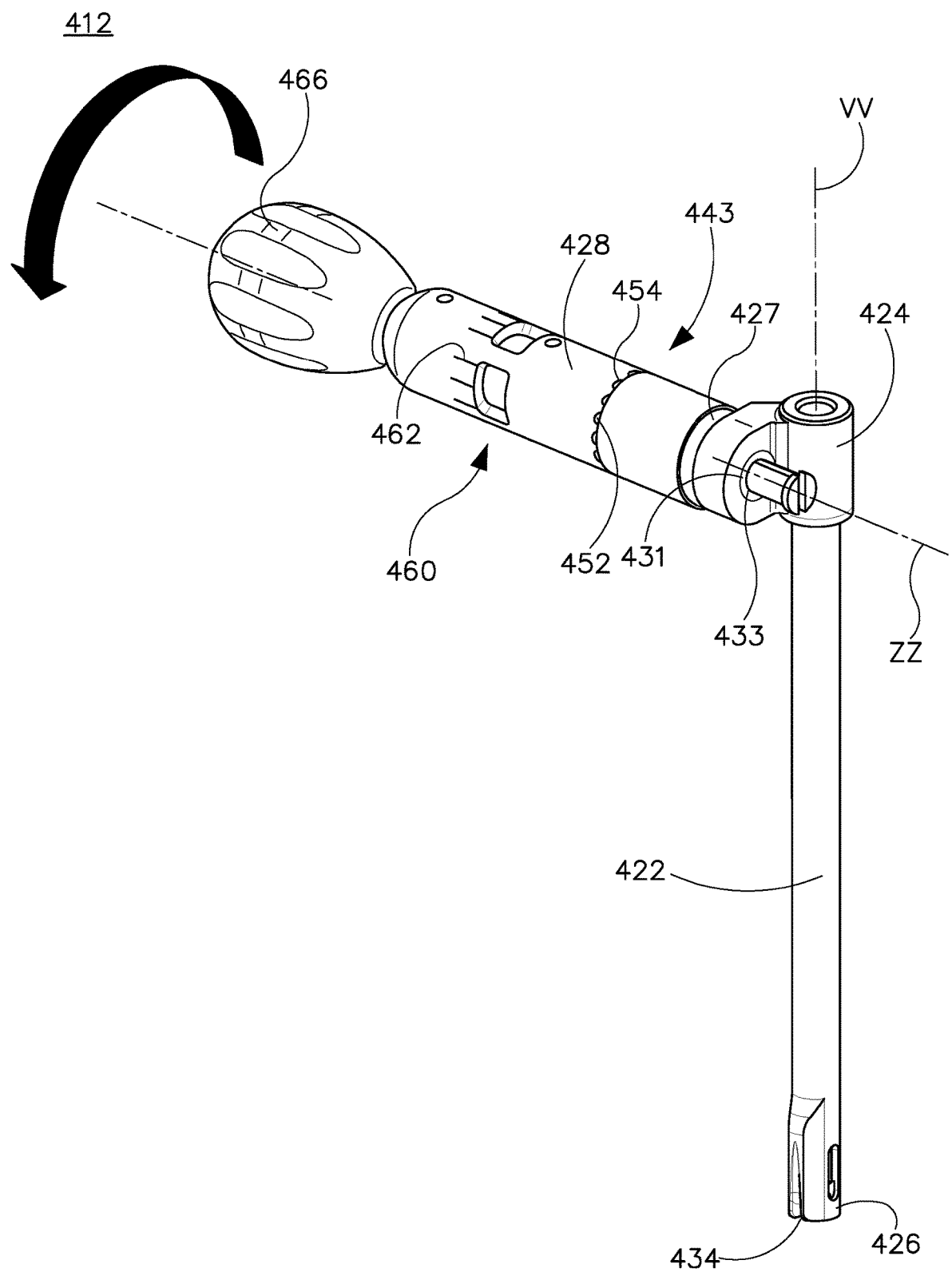
FIG. 46 is a perspective view of one embodiment of components of a surgical system in accordance with the principles of the present disclosure.
Figure 51:
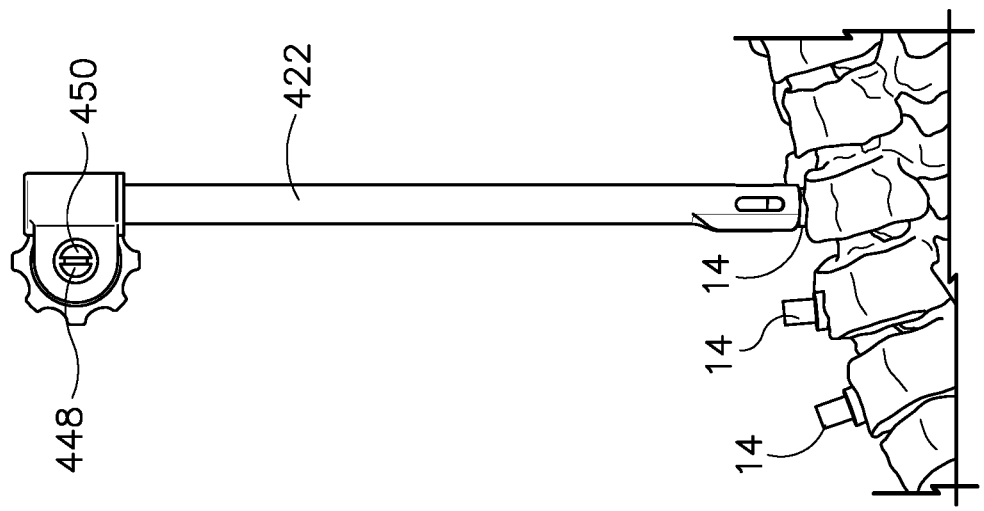
FIG. 51 is a perspective view of the components shown in FIG. 46 disposed with vertebrae.
Figure 50:
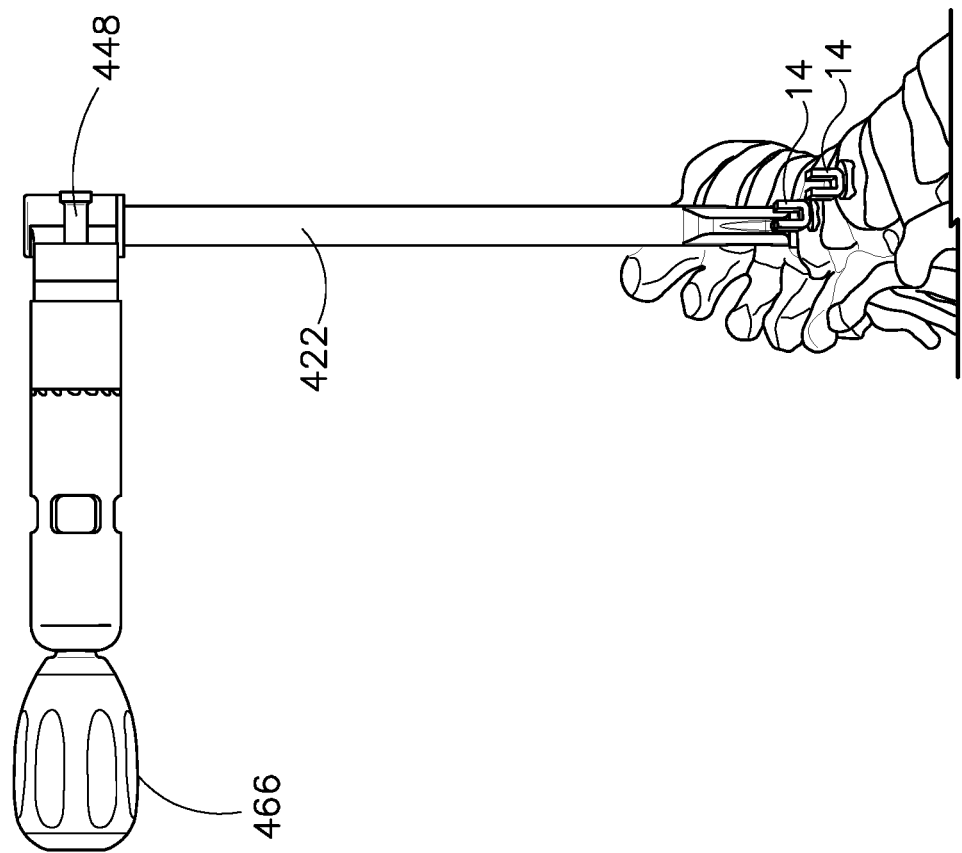
FIG. 50 is a perspective view of the components shown in FIG. 46 disposed with vertebrae.

In one embodiment, as shown in FIGS. 46-53, spinal correction system 10, similar to the systems and methods described above with regard to FIGS. 1-37, includes a tensioner 412, similar to tensioner 12 described herein. Tensioner 412 is configured to apply a rotational tension to tether 16, as described herein. Tensioner 412 includes a shaft 422, similar to shaft 22 described above. Shaft 422 defines a longitudinal axis VV, as shown in FIG. 46. Shaft 422 extends between a proximal portion 424 and a distal portion 426. Distal portion 426 is configured to engage tether 16, and proximal portion 424 is configured to engage a stem 427, shown in FIGS. 46 and 48 and described herein.

Figure 52:
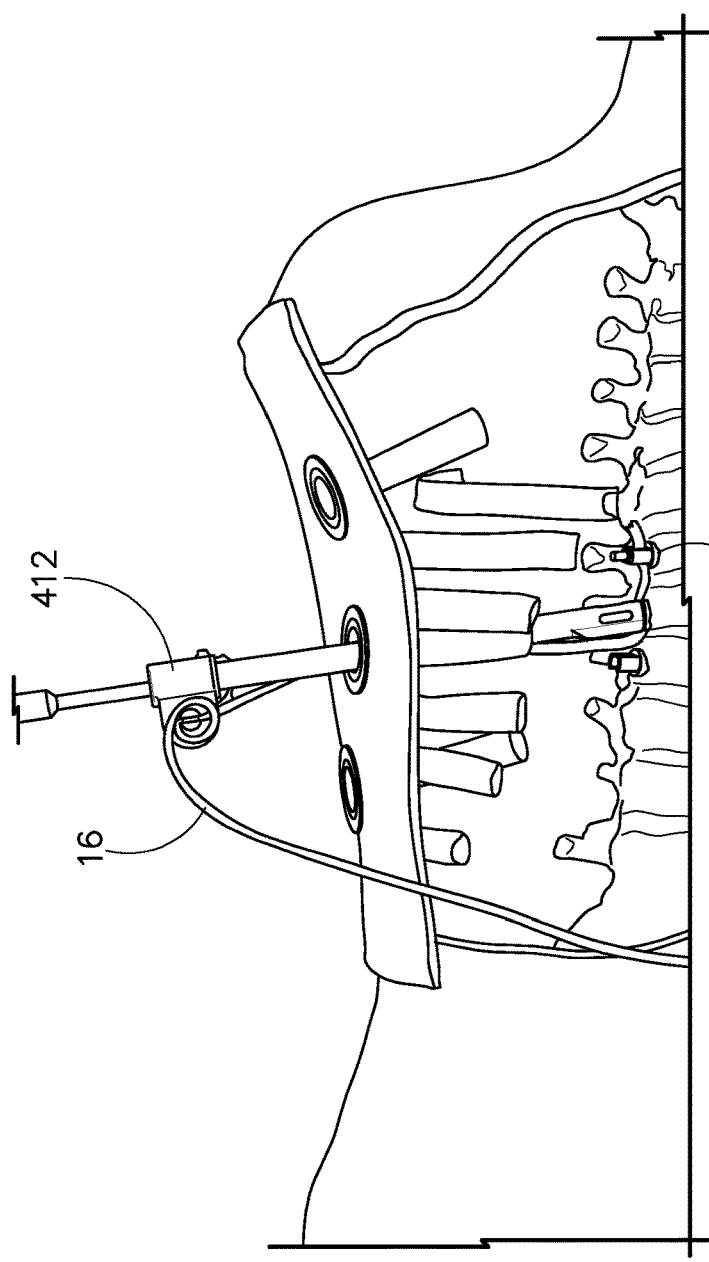
FIG. 52 is a perspective view of the components shown in FIG. 46 disposed with a patient body.

Distal portion 426 includes a guide 430, as shown in FIG. 47. Guide 430 includes a transverse slot 434 engageable with tether 16. Transverse slot 434 is configured to orient, for example, guide tether 16 relative to vertebrae and is engageable with tether 16 to dispose tether 16 with one or more bone fasteners 14 disposed with the vertebrae, as shown in FIG. 52. In some embodiments, slot 434 may comprise various cross-section configurations, for example, cylindrical, round, oval, rectangular, polygonal, irregular, tapered, offset, staggered, uniform and non-uniform. In some embodiments, one or more of the surfaces of slot 434 may have alternate surface configurations, for example, rough, threaded for connection with surgical instruments, arcuate, undulating, porous, semi-porous, dimpled, polished and/or textured.

Stem 427 defines a longitudinal axis ZZ, as shown in FIG. 46. Stem 427 extends between an end 429 and an end 431, and an intermediate portion 435 is disposed therebetween, as shown in FIG. 48. End 429 is configured for engagement with a carriage 428 and intermediate portion 435 is configured for engagement with a ratchet 443. End 431 is configured for engagement with an opening 433 defined from a surface of proximal portion 424, as shown in FIG. 46. In some embodiments, stem 427 may comprise various cross-section configurations, for example, cylindrical, round, oval, rectangular, polygonal, irregular, tapered, offset, staggered, uniform and non-uniform.

Carriage 428 extends between an end 438 and an end 440, as shown in FIG. 48. In some embodiments, carriage 428 may have various configurations, for example, circular, cylindrical, square, oval, rectangular, polygonal, irregular, tapered, offset, staggered and uniform. Carriage 428 is configured for engagement with rachet 443 and a handle 466, as shown in FIGS. 46 and 48. Carriage 428 includes an outer surface that defines an opening, for example, window 460, as shown in FIG. 48. Window 460 is configured to indicate tensioning of tether 16, as described herein. Carriage 428 includes a plurality of graduations 462 disposed on the outer surface and adjacent window 460. The plurality of graduations 462 are configured to indicate rotation of a link 444 of a locking mechanism 442 disposed within carriage 428 that rotates during tensioning of tether 16, as described herein.

Figure 53:
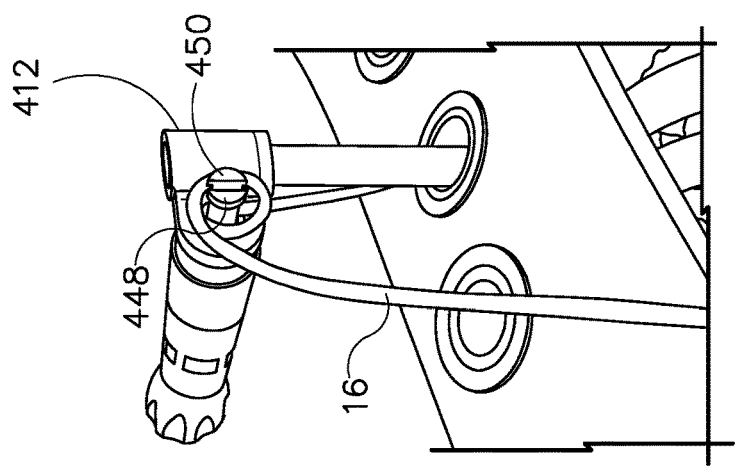
FIG. 53 is a perspective view of components of the system shown in FIG. 46 disposed with a patient body.

Locking mechanism 442 is configured to engage with tether 16 to fix tether 16 with tensioner 412. Locking mechanism 442 includes link 444 that engages with an arm 446. A biasing member, for example, a torsion spring 449 is disposed about a portion of link 444 and a portion of a link 445. Arm 446 includes a grasper jaw 448 and a grasper jaw 450, as shown in FIGS. 48 and 49. Grasper jaws 448, 450 are configured to be positioned between an open/un-locked orientation and a closed/locked orientation. In the locked orientation, grasper jaws 448, 450 engage tether 16 to fix tether 16 with tensioner 412, as shown in FIGS. 52 and 53. In some embodiments, locking mechanism 442 may include penetrating members, for example, a plurality of teeth (not shown). In some embodiments, teeth may have various configurations, for example, round, oval, rectangular, polygonal, irregular, tapered, offset, staggered, uniform and non-uniform.

To position grasper jaws 448, 450 in an open/un-locked orientation, handle 466 is engaged with a threaded opening 439 of carriage 438. Handle 466 is translated in a direction, for example, a forward direction, a compression spring 451 compresses along arm 446, and grasper jaws 448, 450 open. A user disposes a section of tether 16 with grasper jaws 448, 450. To position grasper jaws 448, 450 in a closed/locked orientation, handle 466 is released, and compression spring 451 expands along arm 446, translating handle 466 in a direction, for example, a backward direction, placing grasper jaws 448, 450 in an open/un-locked orientation. To tension tether 16, handle 466 is rotated in a direction, for example, a clockwise direction, causing grasper jaws 448, 450 to rotate and thereby rotatably tension tether 16. Torsion spring 449 contracts around link 444 and a portion of link 445 once tether 16 is taut. Ratchet 443 maintains tension of tether 16 via one way teeth 452 that are engageable with one way teeth 454 of carriage 428, as shown in FIG. 46.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a member including a body engageable with a tether to fix the tether with the body,
   the member further including a distal portion having a guide including an arcuate surface being engageable with the tether;
   an element attached with the distal portion and being rotatable relative to the distal portion; and
   an actuator connected with the member to incrementally tension the tether.

2. A surgical instrument as recited in claim 1, wherein the guide further includes a transverse slot configured to orient the tether relative to vertebrae.

3. A surgical instrument as recited in claim 1, wherein the guide further includes a transverse slot engageable with the tether to dispose the tether with one or more bone fasteners disposed with the vertebrae.

4. A surgical instrument as recited in claim 1, wherein the arcuate surface is engageable with the tether to translate the tether relative to the member.

5. A surgical instrument as recited in claim 1, wherein the body includes a locking mechanism configured to fix the tether with the body.

6. A surgical instrument as recited in claim 1, wherein the body includes a transverse opening defined from a surface of the body.

7. A surgical instrument as recited in claim 6, wherein the surgical instrument includes a threaded cylindrical member connected to the actuator.

8. A surgical instrument as recited in claim 7, wherein the threaded cylindrical member is configured to translate within the body and is viewed via the opening to indicate tensioning of the tether.

9. A surgical instrument as recited in claim 8, wherein the body includes a plurality of graduations disposed adjacent to the opening to indicate translation of the threaded cylindrical member relative to the member.

10. A surgical instrument as recited in claim 7, wherein the surgical instrument includes a biasing member disposed with the threaded cylindrical member and the body, the biasing member being movable within the body for tensioning.

11. A surgical instrument as recited in claim 10, wherein the biasing member is movable in an expanded or contracted orientation.

12. A surgical instrument as recited in claim 1, wherein the body includes a first grasper prong and a second grasper prong configured to engage with the tether.

13. A surgical instrument as recited in claim 12, wherein the surgical instrument includes a ring configured to translate within the body to indicate tensioning of the tether.

14. A surgical instrument as recited in claim 1, wherein the body includes a first grasper jaw and a second grasper jaw configured to engage with the tether.

15. A surgical instrument as recited in claim 14, wherein the body includes one or more biasing members and a ratchet to tension the tether.

16. A surgical instrument comprising:
a shaft including a carriage engageable with a tether to fix the tether with the carriage,
the shaft further including a distal portion having a guide including a slot engageable with the tether and a roller attached with the distal portion, the roller being rotatable relative to the distal portion haft to orient the tether transversely relative to the shaft and/or relative to vertebrae for disposal with one or more bone fasteners; and
a knob connected with the body to incrementally tension the tether.

17. A surgical system comprising:
a flexible tether;
one or more bone fasteners configured for disposal with the tether; and
a surgical instrument including a member including a body engageable with the tether to fix the tether with the body, the member further including a distal portion having a guide including an arcuate surface being engageable with the tether, an element attached with the distal portion and being rotatable relative to the distal portion, and an actuator connected with the member to incrementally tension the tether.

18. A surgical system as recited in claim 17, wherein the surgical instrument includes a counter torque handle.

* * * * *